US008357108B2

(12) United States Patent
Taylor

(10) Patent No.: US 8,357,108 B2
(45) Date of Patent: Jan. 22, 2013

(54) PHYSICAL THERAPY TOOL

(75) Inventor: Alan R. G. Taylor, Cornwall (GB)

(73) Assignee: Advanced Therapy Systems LLC, Ronkonkoma, NY (US)

(*) Notice: Subject to any disclaimer, the term of this patent is extended or adjusted under 35 U.S.C. 154(b) by 1022 days.

(21) Appl. No.: 11/331,486

(22) Filed: Jan. 13, 2006

(65) Prior Publication Data

US 2007/0167888 A1 Jul. 19, 2007

(51) Int. Cl.
*A61H 1/00* (2006.01)
*A61H 7/00* (2006.01)
*A61F 5/00* (2006.01)

(52) U.S. Cl. ............ 601/46; 601/97; 601/101; 601/103; 601/105; 601/107; 601/108; 601/111; 601/136; 601/137; 601/138; 128/845; 606/237; 606/238; 606/239

(58) Field of Classification Search .................... 601/97, 601/101, 103, 105, 107, 108, 111, 133–138; 128/845; 606/237–239
See application file for complete search history.

(56) References Cited

U.S. PATENT DOCUMENTS

| | | | | |
|---|---|---|---|---|
| 4,858,599 | A | 8/1989 | Halpern | |
| 5,092,316 | A | 3/1992 | Taylor et al. | |
| 5,192,316 | A | 3/1993 | Ting | |
| 5,262,615 | A | 11/1993 | Hancock | |
| 5,365,624 | A | 11/1994 | Berns | |
| 5,593,381 | A | 1/1997 | Tannenbaum et al. | |
| 5,653,733 | A | 8/1997 | Keller et al. | |
| 5,794,286 | A * | 8/1998 | Scott et al. | 5/611 |
| 6,503,211 | B2 | 1/2003 | Frye | |
| 6,532,609 | B2 | 3/2003 | Taylor et al. | |
| 7,517,327 | B1 * | 4/2009 | Knight | 601/46 |
| 2003/0212352 | A1 | 11/2003 | Kahn | |
| 2003/0220176 | A1 | 11/2003 | O'Connor | |
| 2004/0097854 | A1 | 5/2004 | Hester et al. | |
| 2004/0158176 | A1 * | 8/2004 | Park | 601/18 |
| 2004/0260215 | A1 | 12/2004 | Kim | |
| 2005/0148906 | A1 | 7/2005 | Skover et al. | |
| 2005/0181917 | A1 | 8/2005 | Dayal | |
| 2005/0222524 | A1 * | 10/2005 | Fielding et al. | 601/98 |
| 2006/0293711 | A1 * | 12/2006 | Keller et al. | 606/238 |

OTHER PUBLICATIONS

International Search Report mailed Oct. 4, 2007, for PCT Application No. PCT/US06/49382, filed Dec. 27, 2006, two pages.
Maitland G.D. et al. eds. (2001). *Maitland's Vertebral Manipulation*. Butterworth-Heinemann: Oxford, UK, 3 pages (Table of Contents).
International Preliminary Report on Patentability mailed on Jul. 15, 2008, for PCT Application No. PCT/US06/049382, filed on Dec. 27, 2006, eight pages.

* cited by examiner

*Primary Examiner* — Clinton T Ostrup
(74) *Attorney, Agent, or Firm* — Morrison & Foerster LLP

(57) ABSTRACT

The physical therapy tools, systems, kits and methods described herein may be used to apply gentle, passive and progressive amounts of pressure (including numerous repetitions of small movements) to achieve therapeutic mobilization of a spinal joint. The tools described herein may include a plurality of pads and actuators, where the pressure within each actuator is controlled so that a continuously varying pressure may be applied to mimic the pressure applied by human hands. These tools may also include a controller and one or more user inputs. The physical therapy tools may be operated at different operating modes (e.g., continuously varying pressure modes, step-pulse high frequency modes, step-pulse low frequency modes) for treating a subject's spine, and may be part of a system or kit. Methods of treating a subject using these physical therapy tools are also described herein.

48 Claims, 17 Drawing Sheets

| Effort | Peak Pressure | Rate | Pressure Cycle time |
|---|---|---|---|
| 1 | 22 PSI | 1 | 2.00 Sec |
| 2 | 28 PSI | 2 | 1.84 Sec |
| 3 | 34 PSI | 3 | 1.69 Sec |
| 4 | 40 PSI | 4 | 1.53 Sec |
| 5 | 46 PSI | 5 | 1.37 Sec |
| 6 | 52 PSI | 6 | 1.22 Sec |
| 7 | 58 PSI | 7 | 1.06 Sec |
| 8 | 64 PSI | 8 | 0.91 Sec |
| 9 | 70 PSI | 9 | 0.83 Sec |

FIG. 9

| Effort | Pressure | Rate | Out Time | In Time ($\Delta t$ ) |
|---|---|---|---|---|
| 1 | 15 PSI | 1 | 15mS | 55mS |
| 2 | 15 PSI | 2 | 15mS | 50mS |
| 3 | 15 PSI | 3 | 15mS | 45mS |
| 4 | 15 PSI | 4 | 15mS | 40mS |
| 5 | 15 PSI | 5 | 15mS | 35mS |
| 6 | 15 PSI | 6 | 15mS | 30mS |
| 7 | 18 PSI | 7 | 15mS | 25mS |
| 8 | 21 PSI | 8 | 15mS | 20mS |
| 9 | 25 PSI | 9 | 15mS | 15mS |

FIG. 12

| Effort | Pressure | Rate | Out Time | In Time ($\Delta t$) |
|---|---|---|---|---|
| 1 | 15 PSI | 1 | 15mS | 1600 mS |
| 2 | 19 PSI | 2 | 15mS | 1410 mS |
| 3 | 23 PSI | 3 | 15mS | 1230 mS |
| 4 | 27 PSI | 4 | 15mS | 1040 mS |
| 5 | 31 PSI | 5 | 15mS | 850 mS |
| 6 | 35 PSI | 6 | 15mS | 660 mS |
| 7 | 39 PSI | 7 | 15mS | 480 mS |
| 8 | 43 PSI | 8 | 15mS | 290 mS |
| 9 | 46 PSI | 9 | 15mS | 100 mS |

FIG. 15

PHYSICAL THERAPY TOOL

TECHNICAL FIELD

This application generally relates to the field of physical therapy, biomechanics, physiology, and particularly to the treatment of the spine.

BACKGROUND

To function correctly, the spine and vertebrae should be free to move throughout their normal range of motion. Spinal function decreases with age and medical condition. With function loss the spine stiffens, excessive wear and tear, stretched ligaments, joint degeneration and pain results. The restoration of function increases and improves spinal range of motion, flexibility and joint mobility.

To restore or improve spinal function, a physician, physical therapist, chiropractor or other health care professional may recommend spinal mobilization. Traditionally spinal mobilization is preformed manually and physical therapists currently employ a number of manual techniques. The most relevant is Maitland mobilization, where the thumbs and hands along with various movements and positioning of the patient effect a mobilizing force upon pairs of vertebrae. These techniques, however, fall far short of focused, precise, joint by joint, gentle, passive and progressive mobilization of the entire spine. As illustrated in FIG. 1, if a force or gentle pressure is applied over the points marked "A" and then over the points marked "B" the vertebral articulation or joint may be rocked or counter rotated back and forth through its normal range of motion successfully delivering mobilizing forces and effecting spinal mobilization. A physical therapist or other health care professional could attempt to apply this pressure with their thumbs or hands however, because the joints of the spine are much bigger and tougher than the therapist's fingers and hands, many therapists would find it difficult if not impossible to apply this technique manually.

Moreover, in addition to the spine's vertebral components, the musculature and reflex muscle activity of the spine is important to back function. Physical therapists believe that with aging and/or chronic back pain and the subsequent development of protective postural responses, guarding, back stiffness and loss of function, the paraspinal muscle groups loose their optimal reflex activity. Just as a patellar reflex will degrade if a leg is immobilized for a long period, so muscle reflexes associated with the stiff or immobile spinal joints degrade. The restoration of these reflexes through repeated and progressive stimulation also contributes to improving spinal function and back health.

Unassisted manual spinal mobilization is difficult, because the forces necessary for manual spinal mobilization requires the application of excessive and uncomfortable pressure from a practitioner's fingers or hands applied to the spinal joints, often for an extended treatment period. Thus, automatic devices have been suggested as a way to assist a practitioner (e.g., a physician, chiropractor, physical therapist, etc.) in mobilizing spinal joints. Unfortunately, most such devices lack the precise control that is beneficial to treatment of spinal joints and cannot adequately reproduce the touch of the practitioner's hand. For example, most known applicators do not allow sufficient control of the rate that the spinal joints are mobilized, or the force used to mobilize the spinal joints. Furthermore, most tools inhibit the practitioner's ability to sense the response of the back and spine to the treatment. Most currently available physical therapy tools provide only crude control (if any) of the rate of application of pressure and the manner in which pressure is applied.

For example, U.S. Pat. No. 5,092,316 to Taylor et al. describes a physical therapy device for treating spinal disorders and represents the state of the art for such physiotherapy tools. This device has reciprocating actuators with feet that can be applied to a pair of vertebra for treatment. The device may include pneumatic logic controlled by an adjustable choke so that the rate at which the actuators are moved is controlled by manually adjusting the choke. U.S. Pat. No. 5,192,316 is essentially a percussion device with two pairs of pistons operating 180° out of phase. One pair of pistons delivers blows over the points marked "A" marked on FIG. 1. As this pair is retracted, the second pair delivers blows over the points marked "B". The blows must, of necessity, be very light. Heavy blows would be injurious. Other examples of existing physical therapy devices may be found in U.S. Pat. Nos. 5,653,733 and 5,262,615 to Keller et al., and U.S. Pat. No. 6,503,211 to Frye. All of the patents listed above are herein incorporated by reference in their entirety.

Ideally, a physical therapy tool for use in treating a spine acts as a virtual extension of the practitioner's hands, allowing the practitioner to easily operate the tool when treating a subject (e.g., adjusting the way that the pressure is applied by the tool including the rate that pressure is applied), and to detect the response of the subject while using the tool. In contrast, most commercially available physical therapy tools permit only limited control, and also inhibit feedback between the subject and the practitioner using the tool.

Precise control is necessary because it allows the practitioner to control the application of treatment. For example, spinal treatment is often difficult to localize. Loss of flexibility may be difficult to correct because interactions between vertebrae are complex, and correction of a problem in one area may exacerbate a problem in another area, or may create a new problem. Further, correction of the new problem (or new problem area) can lead to the reappearance of the original problem. In many cases, effective treatment should be properly localized and scaled based on the nature of a particular subject's spine. A practitioner treating a subject's spine may therefore rely on his or her experience, as well as on feedback from the subject. Furthermore, manipulation applied to specific vertebra may also cause movement of adjacent vertebra. Thus, it is often difficult to increase the intravertebral mobility other than over a substantial period of treatments, using conventional manipulative techniques.

Thus, it would be desirable to provide tools, methods, procedures and kits that overcome many of the difficulties described above, and enable a practitioner to effectively treat the spine of a subject.

SUMMARY OF THE INVENTION

Described herein are physical therapy devices, instruments, tools, systems, methods and kits for treating a subject's spine. Treatment of a spine (or a region of a spine) generally includes the application of pressure or a mobilizing force by a physical therapy tool or by the therapist manual. The physical therapy tools described herein are configured to apply a controllable amount of pressure over time by controlling actuators having one or more pads for contacting the subject. Thus, these physical therapy tools may mimic the application of pressure applied by the fingers and/or the hands.

One central concept of the invention described herein is the use of pneumatic cylinders employed as air springs or cushions. The concept is made plain by the development of air springs used as part of a physical therapy tool through the following steps.

In step 1, a practitioner (e.g., a therapist) may use his or her thumbs to press down over the points marked on FIG. 1A. As their thumbs begin to fail, they may employ the tool illustrated in FIG. 1B. It consists of a handle that the practitioner can grip and two metal rods terminating in pads. Note that the mobilizing effort comes from the practitioner. This tool is a means of transmitting the effort, and substitutes for the practitioner's thumbs. However, the tool may feel harsh, because the metal rods lack the spring of a practitioner's thumbs.

In step 2, we may incorporate a cylinder housing a spring, as illustrated by FIG. 1C. This is an improvement over the tool shown in FIG. 1B, but the spring has a fixed value (e.g., spring constant) and the tool cannot be easily adapted to suit the physique and condition of the patient.

In step 3, we may replace the fixed springs, illustrated in FIG. 1C, with compressed air. The compressed air will act as an air spring or cushion. Because the supply pressure can be varied, the value of the spring can be varied. However, the tool only has two pads. Consequently, in order to work an adjacent pair of vertebrae back and forth in counter-rotation, the practitioner must align the pads to correspond with the points marked "A" on FIG. 1A and then stop and realign the tool to correspond with points "B".

In step 4, we may now progress to a handset comprising of a body that can fit into the palm of the hand and two pairs of cylinders arranged to correspond with points "A" and "B" on FIG. 1A. The cylinders can be alternately energized by means of solenoid-operated valves and a control console can be introduced which contains electronic logic. The cylinders can be caused to cycle so that the "A" pair is energized for a period long enough to allow the practitioner to deliver a mobilizing effort and then the "B" pair is energized for a similar period. Thus, an adjacent pair of vertebrae will be worked back and forth in counter-rotation. However, there is a problem with this arrangement. If the supply pressure is constant, as alternate valves open, the cylinders will deliver a heavy blow before they begin to perform their role as an air spring or cushion.

Thus, we may introduce a means of controlling the supply pressure in proportion to an electrical signal. We may now vary the supply pressure over time and in accordance with a pre-selected program stored in the electronic logic. The solenoid-operated valves may be operated when the supply pressure is very low and the air springs may be energized progressively and drawn down progressively. This may eliminate the percussive blow, and the smooth and progressive cycle greatly assists the practitioner in their task.

In step 5, the size and spacing of the pads can be arranged to cover a wide variation in the size of vertebrae. The practitioner may use the device to work up and down the length of the spine, mobilizing each joint in turn. The procedure is gentle, passive and progressive. As the tool cycles, and the practitioner works his or her way up and down the length of the spine, the practitioner feels the response of each joint and continuously adjusts their touch to tease each joint back to mobility. Practitioners will have a level of feel and control of the handset that transforms it into a tool that provides them with quick, accurate, sensitive, strong methods of applying mobilizing forces.

Typically, the device may provide the practitioner with 'feel' if the palms of the hand are pressed down on the top of the handset while the fingers are relaxed around the body of the tool. However, 'feel' may be lost if the practitioner grips the body of the tool in order to control it. Thus, the device may have a center of push that is separate from the center of action, as illustrated by FIG. 1D.

With each diagonal pair, the practitioner may allow the cylinders to fill and then uses them as cushions through which to deliver a mobilizing effort. Because the pistons are moving in and out, we may consider the mid-point between the four cylinders as the center of action. The palm of the hand is used to press down on the top of the handset and we may consider that this is acting through a center of push. If the center of push is not over the center of action, the handset will travel or step along a line extended from the center of push through the center of action. Thus, with a subtle change of balance, the tool can be caused to travel up or down the spine or be steered from side to side.

In some variations, the tool is so sensitive to subtle changes in balance so that control may become subliminal. Because a practitioner may not need to tightly grip the tool, the tool may provide the practitioner with the 'feel' of the operation of the tool and the subject's spine. Because the practitioner can feel the response of the joints, and because the control may be virtually subliminal, the practitioner may naturally adjust his or her touch to tease each joint back to mobility. Thus, the tool may be used as part of a procedure that is both sensitive and highly interactive.

Additional features and variations of the physical therapy tool, systems including the physical therapy tool, and methods of using the tool are described herein. In some variations, a physical therapy tool for use in treating a spine may include four actuators, two pairs of pads (wherein each pad is connected to an actuator), and a controller configured to cyclically apply continuously varying pressure to each actuator so that the pressure within each actuator increases and decreases at a controlled rate. The pads may be spaced such that they are positioned over two pairs of transverse processes on adjacent vertebra of a subject's back when the tool is applied to a subject. This can allow the tool to apply pressure to adjacent spinal regions. As used herein, a subject may be any subject in need of treatment, including patients, and may refer to humans or animals.

The controller may therefore apply any appropriate amount of pressure over time to the actuators to extend (or retract) the pads. Generally, the controller applies pressure cyclically. This means that the controller repeats the application of a pressure profile to the actuators, resulting in a repeating motion of the actuators. The controller may control each actuator separately (e.g., so that the pressure applied to each actuator or pad is independently controlled), or the controller may synchronize the control of the actuators. For example, the controller may coordinate two pairs of pads so that the two pairs of pads move reciprocally with respect to each other. Thus, alternating pairs of pads may be extended to mobilize a spinal joint. Furthermore, the controller may apply very highly regulated amounts of pressure to the actuators so that the pressure with the actuators accurately tracks the desired pressure profile.

The controller may continuously vary pressure to the actuators. Thus, the actuators are not limited to the application of a "step" of pressure (e.g., on/off control) to the actuator which may result in a blow, as described above. Instead, the pressure profile followed by an actuator may smoothly vary with time (e.g., so that the pressure profile has a curved shape, such as a hemisphere, arc, sinusoid, etc.). A "pressure profile" typically describes the level of pressure (e.g., pressure seen by the actuator) over time. The pressure profile may be repeated with a constant frequency, and the shape of the pressure profile (including the maximum or average level of the pressure) may be regulated by the controller. In some variations, the controller regulates the pressure so that the pressure profile followed by an actuator is a step (e.g., a square wave). Thus, the controller may maintain a constant pressure within an actuator. The controller may regulate the frequency that the step is repeated, as well as the height that the step achieves (e.g., the top of the square wave) and the duration of the step. In some variations, the controller may be configured to regulate the solenoid valve so that the pressure of each pneumatic actuator cyclically follows a curved pressure profile, or a square pressure profile.

The controller is preferably separate from the hand-held applicator. Having a separate controller can allow the applicator to fit comfortably within a practitioner's hand while still allowing control of the applicator. Of course, it should be understood that the tool is not limited to controllers located separately from the applicator.

The pressure within an actuator can be vented through the applicator (e.g., emptying from the actuator through a port on the hand-held applicator), as well as venting through the pressure supply line (e.g., back through the line supplying air to the actuator). The controller may control the venting of air in order to control the pressure profile within an actuator.

The actuators may be pneumatically actuated. For example, the tool may include one or more solenoid valves configured to controllably supply pressure to an actuator. In one variation, the tool may have two solenoid valves, where each solenoid valve is connected to two actuators, and each actuator has a pad (e.g., a foot pad) at its end. Pressure from a pressure source (e.g., compressed air) is regulated by the controller, and the controller instructs the solenoid valve to apply a precise amount of air pressure to the actuator.

The physical therapy tool may include one or more inputs to regulate the tool activity. These inputs may communicate with the controller. Any appropriate input may be used. For example, inputs may be buttons, knobs, dials, switches, keys, toggles, etc. The input may regulate any appropriate aspect of the physical therapy tool, including the power, the pressure profile, the rate of the applicator, etc. For example, the tool may include a cycle duration input to select the duration of a pressure cycle of an actuator. Similarly, the tool may include a pressure input to select the peak pressure of a pressure cycle of an actuator. The tool may also include a step input to select the duration of a pressure cycle over which a constant level of pressure is applied to an actuator to extend a pad. In some variations, the tool includes a dwell input to select the duration of a pressure cycle over which pressure is not applied to an actuator to extend a pad.

The physical therapy tool may include one or more feedback circuits to regulate the pressure applied to the actuators. There may be different levels of feedback. For example, the controller may include a pressure regulator that outputs pressure to the actuators. The pressure regulator may include an internal feedback loop to help maintain the proper level of the pressure output by the pressure regulator. In addition, the tool may include a pressure sensor that detects back pressure from the actuator. The pressure sensor connected to the actuator may be part of a feedback loop to regulate the pressure actually seen by the actuator. The controller may compare the actual (generated) pressure profiles of the tool as it is operated with the intended pressure profile, and may provide feedback to regulate upcoming pressure profiles. Thus, in some variations, the tool includes feedback control logic configured to compare two or more pressure profiles and calculate a scaling multiplier. A scaling multiplier may be used to normalize the pressure profile as the tool is operated.

The tool may also include a memory, and the memory may be connected to the controller. A memory may be used to store a pressure profile of a cycle. For example, the memory may store actual recorded pressure profiles. The controller may compare the actual pressure profiles to each other, or to an ideal pressure profile. The memory may also be used to store pressure profiles (including ideal pressure profiles) or characteristics of pressure profiles to be applied by the controller. For example, the memory may comprise one or more look-up tables of pressure profile characteristics (e.g., maximum pressure, minimum pressure, frequency, etc.) that the controller may access. In some variations, inputs (e.g., user inputs, or preset values) may be used to determine the applied pressure profile.

The controller may also include mode logic for selecting a cycle pressure profile that may be applied to the actuators. Thus, the tool may have different modes corresponding to different types of pressure profiles useable by the tool. Within each mode, the pressure profile may include a range of values defining more precise characteristics. Examples of different modes include: a step-pulse high frequency mode, a step-pulse low frequency mode, and a continuously varying pressure mode. In addition to a general pressure profile, a mode may include characteristic patterns of activation of the actuators (e.g., a mode may control when the pressure profile is applied to each actuator and therefore each pad).

The mode logic may select characteristic properties of a mode (e.g., peak pressure, cycle rate, dwell time, etc.) and/or the mode logic may select which mode to apply, for example, a step-pulse high frequency mode, a step-pulse low frequency mode, and a continuously varying pressure mode. In some variations, the mode logic may also include timing information for switching between modes. For example, the mode logic may determine how long the tool applies a given mode, and may automatically switch between modes after a predetermined time period.

The mode logic may receive user input to select modes. For example, the user may select between a step-pulse high frequency mode, a step-pulse low frequency mode, and a continuously varying pressure mode. Furthermore, the mode logic may receive user input to select the cycle duration, peak pressure applied, dwell time, or combinations thereof, for the pressure profiles applied in the selected mode.

Also described herein are systems for use in treating a spine. A system may include a bench and a physical therapy tool. The bench may be configured for treatment of a subject's spine. For example, the bench may include a bifurcated head support that is movably attached (e.g., it "floats" with respect to the rest of the bench). The height of the bench may be adjustable to allow the practitioner using the tool on a subject to have comfortable access to the subject's back (spinal region). Thus, the bench may be supported by a telescoping support. For example, a single telescoping support may be used to support the bench, and the bench may include a control (e.g., a foot petal) for adjusting the height by the practitioner. In some variations, the bench comprises arm rests. The arm rests may be separately adjustable, or they may be fixed in position. In some variations, the arm rests are below the region of the bench that supports a subject's torso. The bench may also include a leg extension.

The adjustable bench may have a curved, body-supporting region so that a subject's torso may be supported at a different incline than the subject's lower body. In some variations, the bench includes a deck at least partly surrounding the bench. The practitioner may stand on the deck, for easy access to the subject. Components of the system (e.g., wires, cables, motors, etc.) may be stored beneath the deck for protection and to allow convenient access.

The deck may also include an adjustable stand for supporting at least part of the physical therapy tool, and the adjustable stand may be moved from one side of the bench to the other side of the bench. For example, the adjustable stand may include a sliding arm that rotates around a portion of the deck and allows repositioning of the stand on one side or the other of the deck.

Also described herein are methods of treating a subject's back. A method of treating a subject's back may include placing a tool against the subject's back (where the tool includes at least two actuators and two pairs of pads, and wherein each pad is connected to an actuator) and operating the tool in a first mode so that each actuator is cyclically actuated by a continuously varying pressure. The step of operating the tool in the first mode may include operating the tool so that the pressure profile of any of the actuators rises and falls in a semicircular curve. The first mode may have a pressure cycle time of between about 0.8 sec and about 2.0 sec. This first mode may also be referred to as a "continuously varying pressure mode."

The method may also include the step of operating the tool in a second mode, wherein each actuator is cyclically actuated by a step increase in pressure. The second mode may be referred to as a "step-pulse low frequency mode," and may maintain a peak pressure. The second mode may maintain the peak pressure for about 15 ms of a pressure cycle time between about 100 ms and about 1.6 sec (e.g., the cycle time may be about 1.6 sec, 1.41 sec, 1.23 sec, 1.04 sec, 850 ms, 660 ms, 480 ms, 290 ms, or 100 ms). In some variations, the method may also include a step of switching between the first mode and the second mode.

The method may also include the step of moving the tool along the subject's spine. In some variations the method includes a step of operating the tool in a third mode (which may also be referred to as a step-pulse high frequency mode). In the third mode, each actuator is cyclically activated by a step increase in pressure. The third mode can maintain a peak pressure. In the third mode, the peak pressure is maintained for a duration of about 15 ms, and the pressure cycle time is between about 15 ms and about 55 ms. Thus, the pressure cycle time may be about 15, 20, 25, 30, 35, 40, 45, 50, or 55 ms.

The method may also include a step of applying a lubricant to the subject's back or to the pads of the tool. Lubricant may also be applied to the back of the tool (e.g., the region gripped by the practitioner). The lubricant may be any lubricious material, particularly lubricants suitable for contacting a subject's skin. For example, the lubricant may comprise a water-based surfactant. Oil-based lubricants may also be used. In some variations, the method may also include maintaining or adjusting a pre-selected or desirable temperature of the subject's back (e.g., the tool may include heating or cooling components for regulating the temperature of the tool or of the subject's back).

Also described herein are methods of treating a subject that include placing a physical therapy tool against the subject's back, operating the tool in step-pulse high frequency mode so that each actuator is cyclically activated by a step increase in pressure (wherein the step-pulse high frequency mode maintains a peak pressure for a duration of about 15 ms of a pressure cycle time of between about 15 ms and about 55 ms), switching from the step-pulse high frequency mode to a step-pulse low frequency mode so that each actuator is cyclically activated by a step increase in pressure (wherein the step-pulse low frequency mode maintains a peak pressure for a duration of about 15 ms of a pressure cycle time of between about 100 ms and about 1.6 sec), and switching from the step-pulse low frequency mode to a continuously varying pressure mode so that each actuator is cyclically actuated by a continuously varying pressure and a pressure cycle time of between about 0.8 sec and about 2.0 sec.

In some variations, this method may also include a step of repeatedly switching between the continuously varying pressure mode and the step-pulse low frequency mode. The method may also include a step of switching from the step-pulse low frequency mode to the step-pulse high frequency mode and removing the tool from the subject's back.

Also described herein are kits for treating a spine. The kit may include a physical therapy tool for use in treating a spine. The kit may also include a lubricant appropriate to apply to a subject's back. In some variations, the kit includes instructions describing at least the operation of the physical therapy tool. The kit may also include a bench, such as an adjustable bench.

BRIEF DESCRIPTION OF THE DRAWINGS

The accompanying drawings, which are incorporated in and form a part of this specification, illustrate embodiments of the invention and, together with the description, help to explain the principles of the invention.

FIG. 9 shows a look-up table illustrating various peak pressures and pressure cycle times for some variations of the continuously varying pressure mode, as described herein.

FIG. 12 shows a look-up table illustrating various peak pressures and dwell times for some variations of the step-pulse high frequency mode, as described herein.

FIG. 15 shows a look-up table illustrating various peak pressures and dwell times for some variations of the step-pulse low frequency mode, as described herein.

DETAILED DESCRIPTION

The physical therapy tools, systems, kits and methods described herein may be used to mobilize, or manipulate, the musculoskeletal joints of the spine. For example, a practitioner may use these tools to treat a subject's spine (e.g., to restore elasticity of the spine) by manipulating the spinal musculoskeletal joints (spinal joints). In general, the physical therapy tools described herein are electromechanical devices that can assist the practitioner by controllably applying pressure to a subject's back to help mobilize spinal joints. These tools typically include a plurality of pads that can be used to apply pressure to spinal joints in way that may be effectively controlled. For example, the tools may be used for the application of gentle, passive and progressive amounts of pressure (including numerous repetitions of small movements) to achieve therapeutic mobilization of a spinal joint, as described below.

Figure 1A:
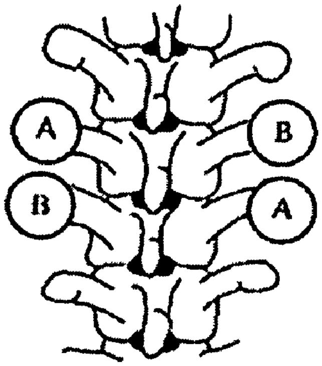
FIG. 1A shows planar view of a section of human vertebra.
Figure 1B:
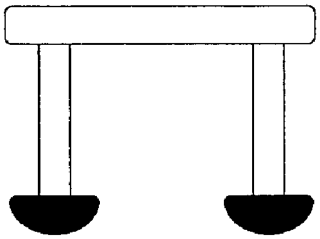
FIG. 1B shows an example of a physical therapy tool.
Figure 1C:
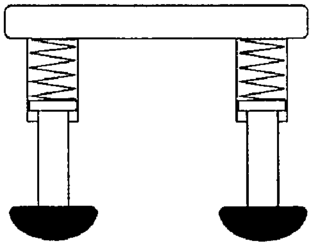
FIG. 1C shows another example of a physical therapy tool.

Thus, the tools, systems, methods and kits described herein may be used to assist in the mobilization of spinal joints. The term "mobilization" refers to the movement of individual joints through their normal range of motion. For example, mobilization of the joints of the spine is described by Maitland (e.g., see G. D. Maitland, E. Hengeveld, K. Banks, and K. English, editors, Maitland's Vertebral Manipulation, 6th edition, Butterworth Heinemann (2000), herein incorporated by reference in its entirety). As taught by Maitland, a practitioner uses his or her hands, and fingers to press the spinous or transverse processes of adjacent pairs of vertebrae. FIG. 1A illustrates adjacent vertebrae with the lateral ends of the transverse processes marked as pairs A and B. If a force is exerted upon the points marked A, g a mobilizing torque is produced within the joint. He or she then presses down over the points marked B. Thus, the joint is worked back and forth in counter-rotation.

The physical therapy tools described herein may effectively mimic the mobilizing forces effected by the manual action taught by Maitland, because the tools can cyclically apply continuously varying pressure to actuators to move pads so that the pressure within each actuator increases and decreases at a controlled rate, smoothly and controllably assisting a practitioner to manipulate a subject's spinal joints.

In conjunction with the figures, the disclosure below describes the physical therapy tool, including the component parts, the operation of the physical therapy tool, including operating modes, systems for treating a subject's spine that include these physical therapy tools, and methods of treating a subject using these physical therapy tools.

Physical Therapy Tool

Figure 2:
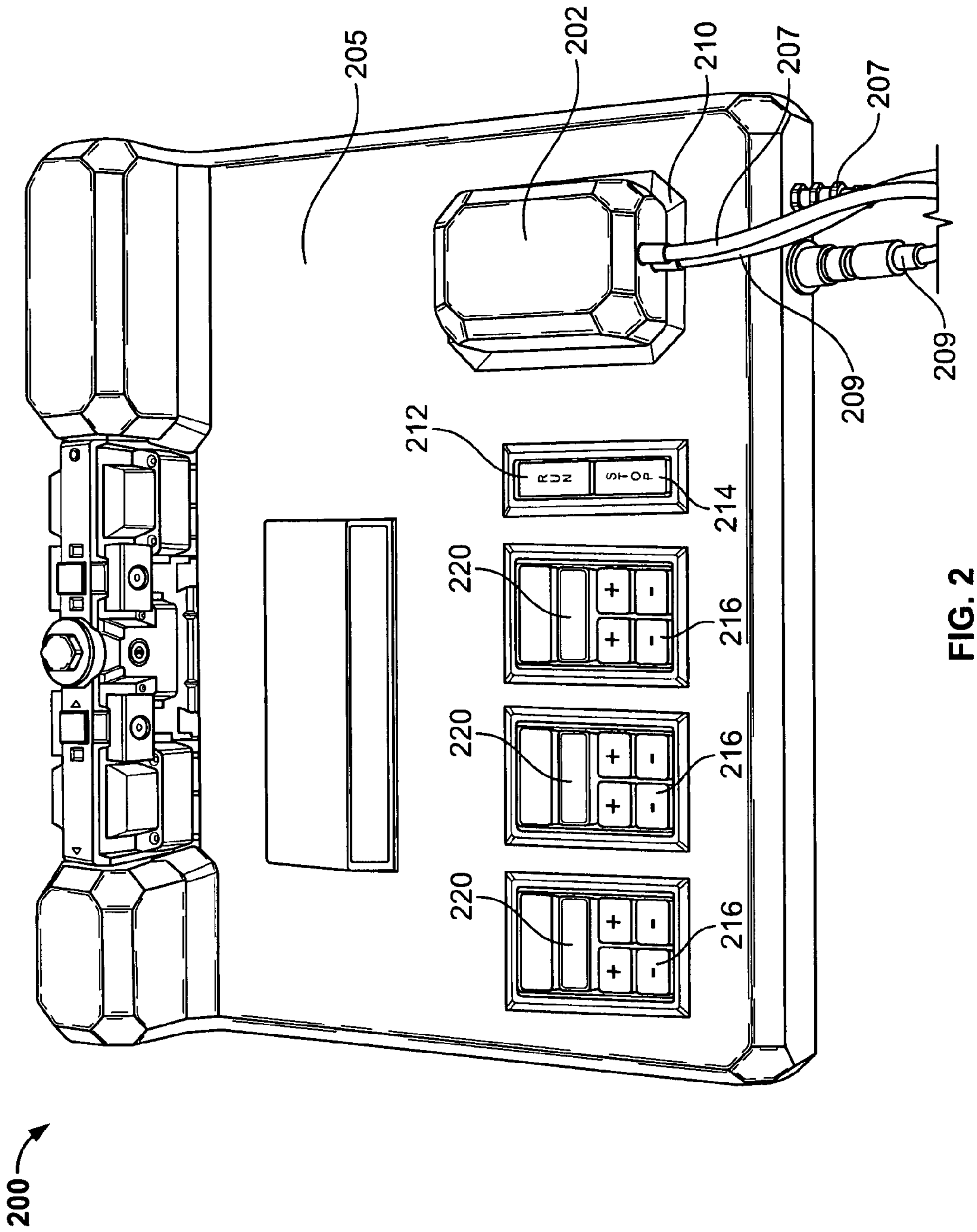
FIG. 2 illustrates one variation of a physical therapy tool as described herein.

FIG. 2 shows one variation of a physical therapy tool as described herein. In FIG. 2, the physical therapy tool 200 includes an applicator 202 connected to a console 205. The console connects to the applicator through an air line 207 and a control line 209, which may be any desirable length. The applicator shown in FIG. 2 is a hand-held applicator that may be manipulated by a practitioner applying the physical therapy tool (e.g., the applicator portion of the tool) to a subject. Some variations of the physical therapy tool do not include a separate console. For example, the tool may include only an applicator.

The physical therapy tool 200 may also connect to a power source (not shown) and a pressure source (e.g., an air compressor, not show). In some variations, the console also includes a cradle 210 in which the applicator may rest. The tool may also include one or more inputs to permit input of user instructions. For example, In FIG. 2, the console includes buttons for starting 212, stopping 214, or selecting control values for the operation of the device 216. The device may also include one or more outputs, including LEDs, output displays, indicators, or the like, for showing the status of the tool (e.g., on/off status, the air pressure, mode information, timing information, applicator rate, etc.). Outputs and inputs may be located on the console, the applicator or any other portion of the physical therapy tool, or a system including the physical therapy tool.

The applicator 202 shown in FIG. 2 can be held in one or both of a practitioner's hands. Thus, the applicator may be hand-held. In some variations, the applicator is shaped so that it may be comfortably held. As described below, the hand-held applicator is generally balanced so that the practitioner may lightly grip the applicator. Thus, the applicator does not need to be tightly gripped (e.g., with the fingers of the hand). The practitioner's hand may be relaxed against the applicator, preventing strain on the practitioner's hands.

Figure 3:
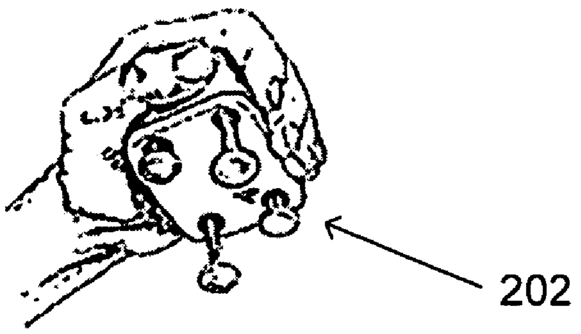
FIG. 3 shows a perspective view of an applicator of a physical therapy tool as described herein.

The applicator may include grips (e.g., a shaped surface) to improve the practitioner's hold on the device, even when using a light touch. The applicator may also include textured or treated surfaces to improve grip, or for more comfortable operation. Thus, the applicator may be configured to be held and operated by a practitioner using one or both hands. For example, the applicator may be of an appropriate size and weight so that it can be easily operated. FIG. 3 shows an example of an applicator 202 held in a hand. As shown in FIG. 2, the applicator 202 may be connected to the console by one or more pressure and/or electrical connections 207, 209. These connections may include tubing, cords, or the like, and may be of any appropriate length so that the practitioner can conveniently reach the subject while operating the tool. If the tool includes more than one connection, the connections may be linked together (or otherwise combined) so that the connection does not interfere with the manipulation of the applicator.

Figure 4:
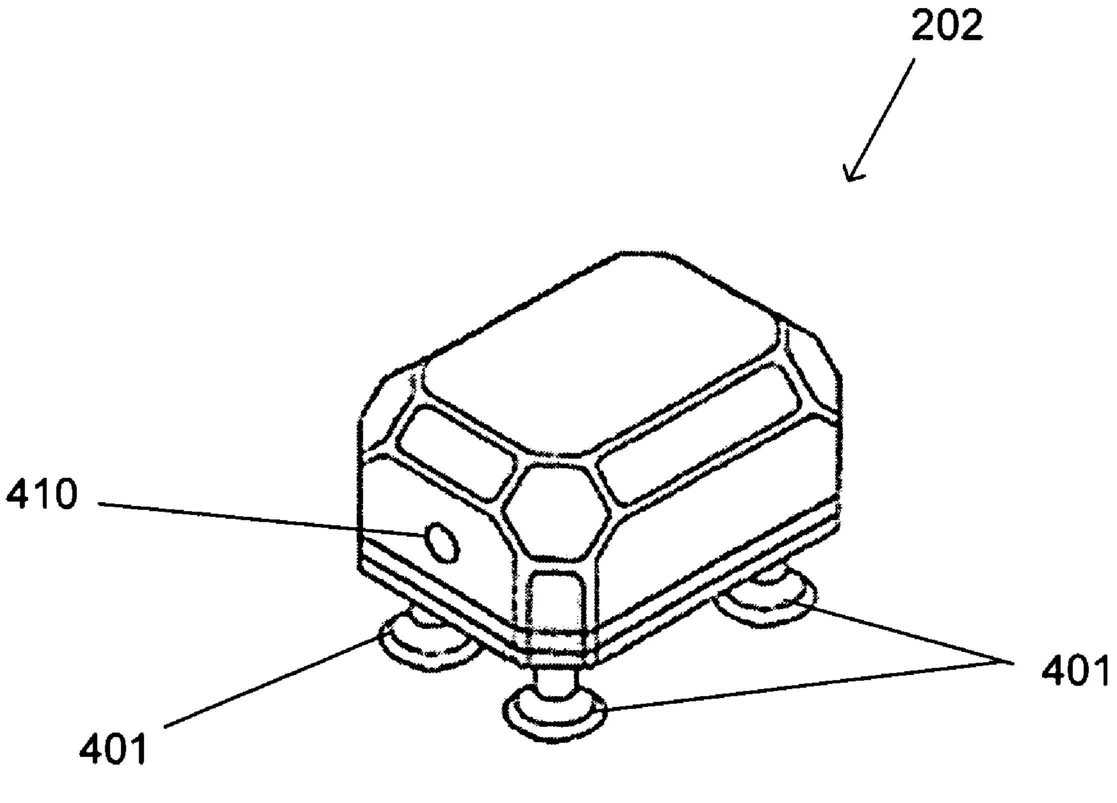
FIG. 4 shows another perspective view of an applicator of a physical therapy tool as described herein.

FIG. 4 shows another variation of the hand-held applicator portion of the physical therapy tool. Pads 401 project from one or more surfaces of the applicator, so that the pads may be held against a subject. As described more fully below, pressure may be applied to the actuators to extend the pads, and the pressure driving the pads may be transferred to a subject by a practitioner holding the applicator 202. In FIG. 4, three pads 401 (of four) are visible in the perspective view of the applicator 202. The upper portion of the applicator includes flat surfaces having smoothed or rounded edges that allow a practitioner to hold the applicator, as shown in FIG. 3.

Figure 1D:
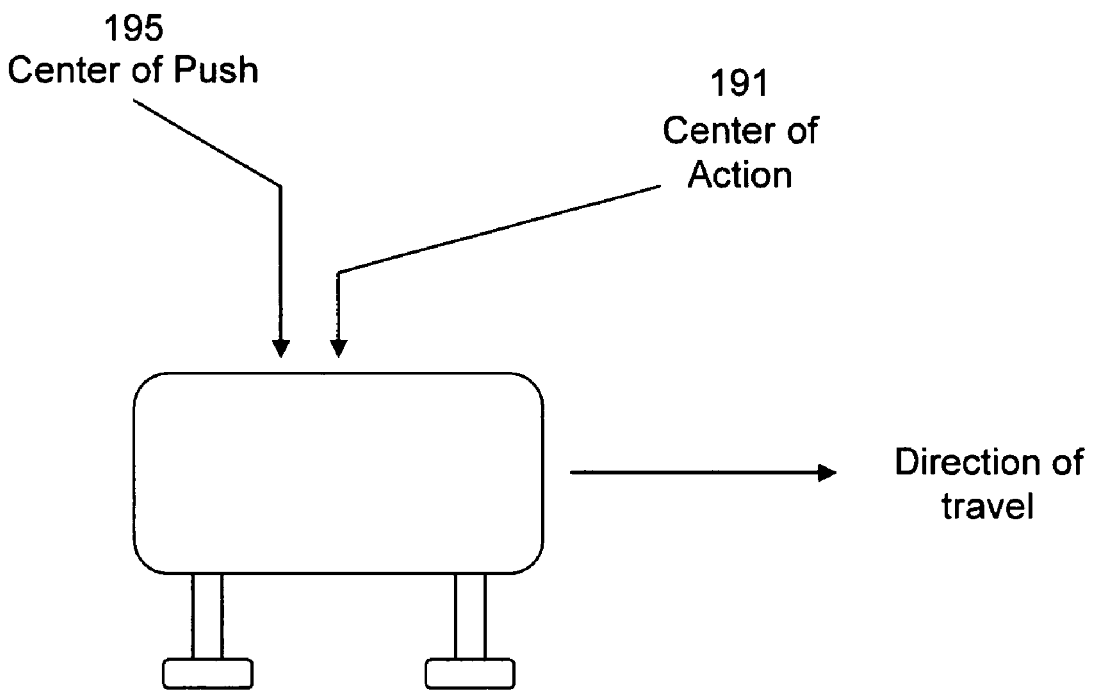
FIG. 1D shows the balance of one variation of a physical therapy tool, as described herein.

As illustrated in FIG. 1D, the applicator may be balanced so that a practitioner can easily (and gently) guide the applicator over a subject's back. The applicator may include a center of balance or a center of action 191. The center of action is the point where the forces applied by the movement of the pads and actuators during the cyclic operation of the tool are balanced. In the example shown in FIG. 1D, because the four pads are each connected to an actuator moving up and down, the mid-point between the four pads is the center of action. Because the applicator is balanced (e.g., the movement of the pads and actuators is balanced), a practitioner may move the running applicator by applying a gentle pressure through a center of push 195 that is offset from the center of action 191. For example, the center of push may be located by the heel of the practitioner's hand when holding the applicator. Note that the applicator may be held against the subject by the practitioner (e.g., applying force perpendicular to the back of the applicator, or the direction of the motion of the pads). The amount of force applied by the practitioner against the applicator may be determined by the experience of the practitioner and the feel of the device against the spine, as descried earlier.

By gently shifting the force applied to the applicator to the center of push 195, the practitioner may "walk," move or advance the applicator up or down along the subject's back. Because the applicator is balanced, the applicator may be intuitively moved by the practitioner when the practitioner shifts the center of push on the applicator away from the center of action. The applicator moves in a direction extending from the center of push 195 through the center of action 191, as indicated in FIG. 1D.

The applicator in FIG. 4 also includes a pressure vent 410, through which pressure (e.g., air pressure from the actuators) may be vented. In some variations, the applicator may also include one or more inputs or controls for controlling the tool. For example, the applicator may include an on/off button, an input to switch the mode that the device is operating in, an input to control the peak pressure, the cycle duration, cycle rate, or dwell time, or the like. The applicator may also include one or more sensors for detecting user status. For example, the applicator may include a sensor for determining when the applicator is being held by the user.

Figure 5:
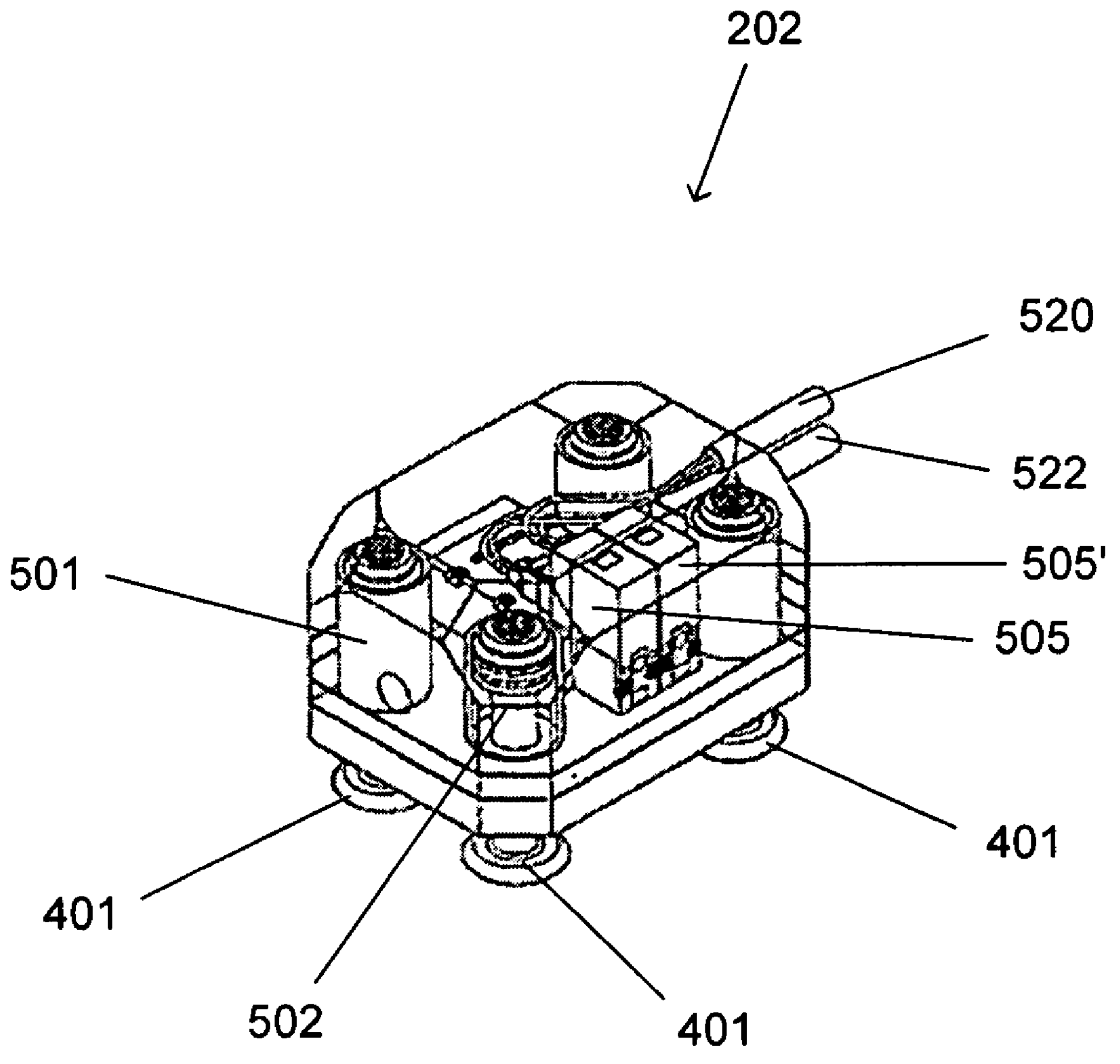
FIG. 5 shows a partially transparent view of the applicator of FIG. 4, showing internal components of the applicator.

FIG. 5 shows one variation of the applicator in which the outer cover has been made transparent, revealing four actuators 501 that are each connected to a single pad 401. Thus, the applicator 202 shown in FIG. 5 also includes two solenoid valves, 505, 505' that are connected via electrical connection 520 to a controller in the console (not shown). The solenoid valves are described in more detail below, and are connected to a pressure line 522 so that the pressure to each actuator may be regulated.

The pads 401 may be spaced in any appropriate manner on the tool. In particular, the pads may be spaced so that the tool can be applied to a subject's back and the pads will remain positioned over two pairs of transverse processes on adjacent vertebra. The distance between the lateral ends of the transverse processes of adjacent pairs of vertebrae varies from spinal level to spinal level and from subject to subject. However, the size of the pads and the distance between the pads can be chosen to cover a wide variation of spaces. In some variations, the pads may be adjustably spaced. For example, the actuators (or just the pads) may be movable so that they can be adjusted to fit the spacing of the lateral ends of the transverse process of a variety of subjects. Once positioned, the pads (or the actuators) may be locked into position. Thus, the pads may be placed so as to correspond with the points marked A or B on FIG. 1.

The pads shown in FIGS. 2-5 are rounded disks; however, the pad may be of any suitable geometry (e.g., elliptical, rectangular, crescent, etc.). In some variations, the pads have a flat contact surface (the surface that contacts the subject's back). The contact surface may have any appropriate shape. For example, the pads may have a curved (e.g., semicircular) cross-section. The contact surface may also have any suitable texture (e.g., smooth, rough, dimpled, etc.). Furthermore, the pads may be made of any appropriate material. For example, the pads may be made of an elastic material (e.g., a rubber, such as a silicone rubber, a polymeric material, etc.), an inelastic material (e.g., metals, hardened polymers, or the like), or a lubricious material (e.g., Teflon, hydrophobic or hydrophilic lubricants, or the like). The pads may be coated with one or more materials (e.g., fabrics, etc.). In some variations, the pads may be removable. Thus, the pads may be replaceable, washable and/or sterilizable.

Actuators

The actuators may comprise pneumatic actuators that respond to the application of pressure, such as air pressure. Generally, a single pad is connected to a single actuator (e.g., in a one-to-one correspondence), which allows the pressure profile in each actuator can be individually controlled. However, actuators connected to multiple pads are also within the scope of the tools described herein.

The pad may be extended (or retracted) by the pressure within the actuator. FIG. 5 illustrates four double-acting pneumatic actuators 501 that are each attached to a pad 401. These actuators each include an actuator piston 502 that is movable to extend or retract the pad. In general, the physical therapy tools described herein may control the pressure applied to each actuator with precision. Controlling the pressure within the actuator provides therapeutic effects.

Any appropriate arrangement of actuators may be used. FIGS. 2-5 show an applicator having four actuators each connected to a pad. The arrangement of the actuator within the applicator does not have to correspond to the arrangement of the pads, since the pads may be connected to the applicators in any appropriate manner. For example, pads may be connected to actuators by a long connector allowing the actuator to be located away from the pad (or pads).

Although the application of pressure to the actuators may cause the extension and retraction of the pads, one possible therapeutic advantage of the physical therapy tool results from the regulation of the pressure profile within the actuator, and not simply the movement of the pads against the subject. Because the pressure profile within the actuators may be regulated by the tool (e.g., by the controller), the tool may mimic the mobilizing force applied by a practitioner's thumbs when used by a practitioner. For example, the thumb is springy. Thus, the actuator and pads described herein may comprise a spring element. In particular, the actuator may comprise an air spring (or air cushion). The actuator may therefore be configured to replicate the spring-like effect of a practitioner's thumbs (or other fingers). Thus, the actuator extends with only a minimum amount of pressure, and will remain extended as long as any force opposing the pressure from the actuator does not exceed the pressure within the actuator. Thus, when the applicator is applied against a subject's back, pads (e.g., the pads that are extended by their actuators so that they contact the subject's back) exert force proportional to the amount of pressure within the applicator against the area of the subject's back that the pad contacts. Because the entire applicator is typically held against a subject's back by the practitioner (who is applying force to keep the applicator positioned against the subject's back), the amount of pressure applied to the subject's back may depend upon the pressure applied by the practitioner in addition to the pressure applied by the tool.

The amount of pressure per unit time (the pressure profile) of each actuator may be controlled by the physical therapy tool. In particular, the amount of pressure applied into the actuator may be continuously variable. In some variations, the pressure profile within the actuator is regulated by one or more feedback loops. For example, the total pressure within the actuator may be regulated by measuring the back pressure from within one or more of the actuators. Thus, a pressure sensor may be positioned between the actuator and the pressure supply, or within the actuator. For example, a pressure sensor may be positioned between the pressure supply and the solenoid valve, or between the solenoid valve and the actuators that the solenoid valve provides pressure to. In some variations, the solenoid valve may include a pressure sensor as part of the valve. Thus, whereas most mechanical springs have a fixed value or stiffness, the spring force applied by a pneumatic actuator may be regulated so that it is proportional to the supply pressure. Consequently, the value of the spring can be matched to the build of a subject, and can adjust based on the pressure provided by the practitioner.

Although the figures and examples described above illustrate pneumatic (e.g., air) actuators, any appropriate type of actuator can be used. For example, the tool may include hydraulic actuators, electromagnetic actuators, magnetic actuators (e.g., solenoids), mechanical actuators, or some combination thereof. Furthermore, the actuators shown in the figures are linear actuators, which typically move in and out. In some variations, the actuators may move in different and additional directions (e.g., size to side, in rotation, etc.).

Figure 6:
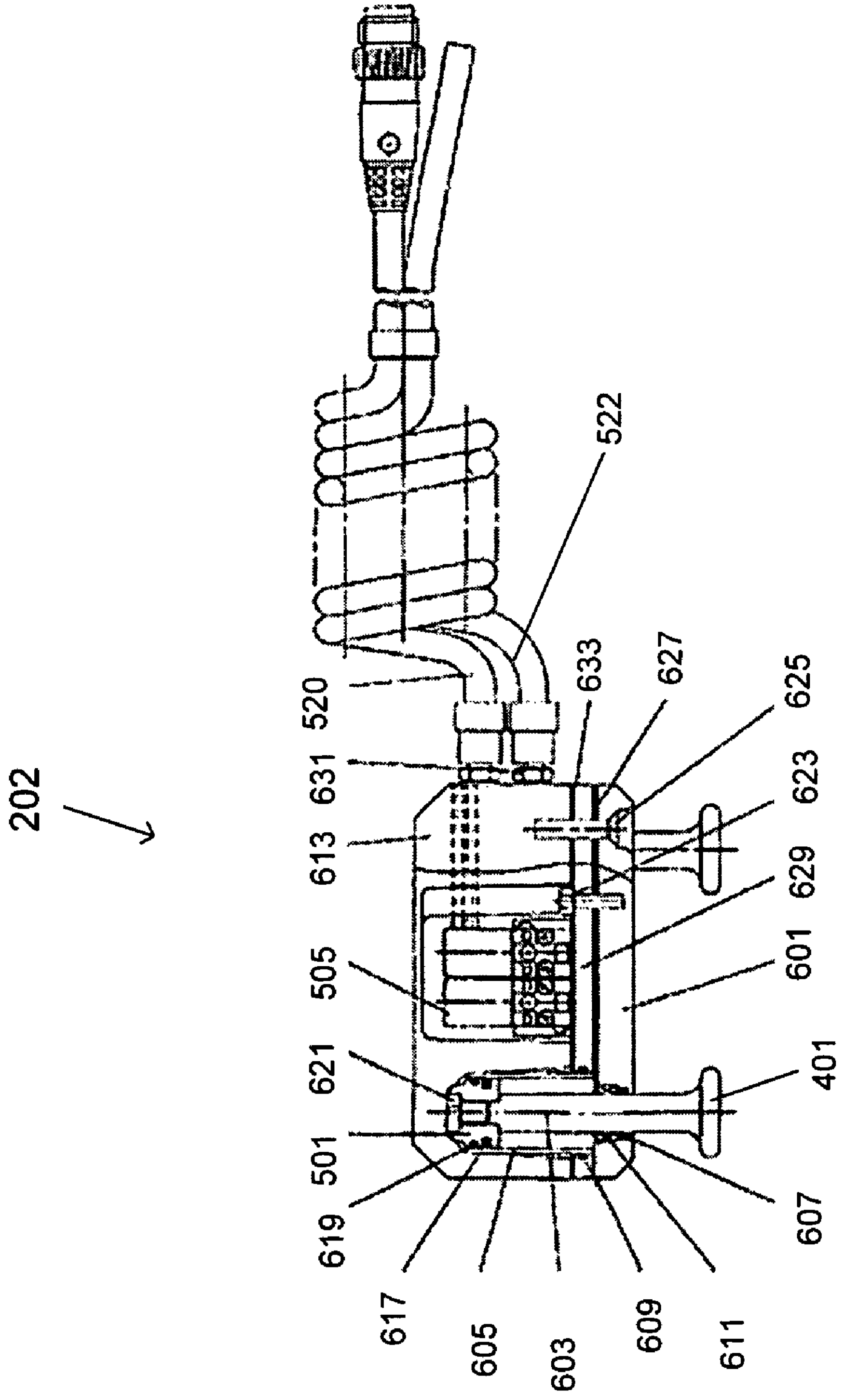
FIG. 6 shows a cross-sectional view of an applicator and a connector as described herein.

FIG. 6 shows a partial cross-sectional profile view of one variation of an applicator and connector that may be connected to a console, as shown in FIG. 1. In FIG. 6, the applicator 202 includes pneumatic actuators 501 that are each connected to a pad 401. The actuator includes a piston 603 within the cylindrical housing 605. Pressure within the housing is maintained by seals 607, o-rings 609, and bushings 611 where the piston rods pass through the bottom cover 601 of the applicator. The upper portion of the actuator includes elements that may help cushion the effect of the actuator movement (e.g., movement of the piston and pad) against the rest of the applicator and particularly the practitioner's hand. For example, the actuator has a piston seal 617, a wear ring 619, and a damper 621. As shown in FIG. 5, a solenoid valve 505 is included within the body of the applicator and shown connected to an electrical connection 520 and a pressure connection 522. The electrical and pressure connections are shown as coiled tubes that connect to the applicator by fittings 631. A cover 613 encloses the upper portion of the applicator and may be used as a grip (e.g., for holding the applicator as described above).

As previously described, the pressure within an actuator may be regulated by a controller. This may allow greater efficiency, accuracy and repeatability.

Controller

The physical therapy tools described herein may include a controller for regulating cyclic application of pressure within each actuator. The controller may also receive and process user (e.g., practitioner) input, and provide output indicating the status of the tool, or a part of the tool. In some variations, the controller may also coordinate transitions between different modes of operation of the physical therapy tool corresponding to different cyclic pressure profiles.

A controller may include hardware, software, or any combination thereof. For example, a controller may be a printed circuit board (PCB). In some variations, a controller includes a processor and one or more memories (e.g., EPROM, RAM, ROM, etc.). The controller may execute control logic, such as mode logic (e.g., for selecting a mode of operation and/or specifying the parameters of a pressure profile of a mode of operation), feedback control logic (e.g., for regulating the pressure within one or more actuators), etc.

The controller may be part of any portion of the physical therapy tool, including the console and/or the applicator. The controller may also receive information from user inputs or from memory elements to control the physical therapy tool. Any appropriate input may be used, including inputs for controlling or regulating power (on/off), mode (e.g., type of pressure profile), pressure profile (e.g., peak pressure, dwell duration, pressure cycle duration, etc.), or the like. Any appropriate type of input may be used (e.g., buttons, switches, keyboard, toggles, dials, etc.), including remote inputs. For example, the physical therapy device may include telemetry, e.g., for wireless communication or control. Furthermore, the controller may also include one or more outputs for communicating with a practitioner, or for storing information. Thus, the device may include one or more displays, LEDs, etc.

The controller may regulate the pressure applied to an actuator by one or more valves. For example, a solenoid valve may be used, particularly with pneumatic actuators. In one variation, a solenoid valve that can controllably supply between about 10 psi and about 100 psi of pressure to an actuator is used. This solenoid valve may increase and decrease pressure within the solenoid valve at a controlled rate. For example, the solenoid valve may include inputs from the controller that allow regulation of pressure by the solenoid valve so that the pressure within an actuator is maintained at any pressure between about 10 and 100 psi for a desired increment of time (e.g., greater than about 1 ms).

Figure 7:
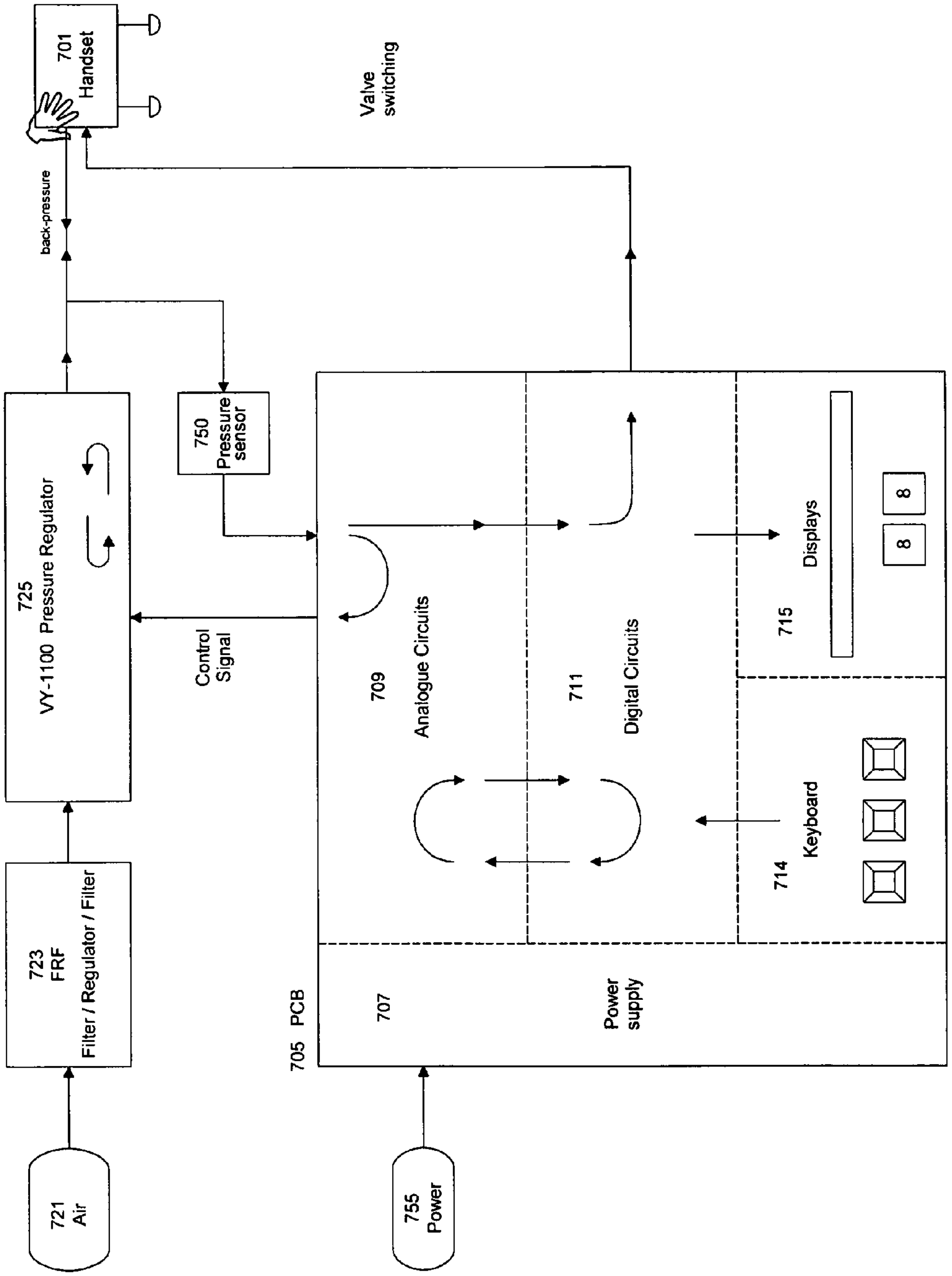
FIG. 7 shows a block diagram describing one variation of a controller for a physical therapy tool, as described herein.

FIG. 7 shows a block diagram including one variation of a controller for a physical therapy tool. In the device depicted in FIG. 7, the physical therapy tool includes a handset applicator 701 that receives control signals and compressed (pressurized) air. The controller includes a printed circuit board (PCB) 705. In FIG. 7, the controller receives power 755 from a power source (e.g., line power from a typical wall line), and uses this power to run the controller, and may distribute power to any other components of the tool requiring electrical power, after conditioning the power through a power supply 707. The controller also includes analog 709 and digital 711 circuit components. Thus, pressure at various nodes (e.g., from the pressure sources such as the air compressor 721, filters 723, pressure regulators 725, applicator lines, actuators 701, etc.) may be detected by the analog circuits, which may respond to regulate the pressure based on pre-set or user-defined parameters. Some (or all) of these analog signals may be converted to digital signals for further processing. For example, the controller may include a digital memory (not shown) to store (e.g., a look-up table) or provide parameters for regulating the pressure at various nodes. The controller may also include logic for controlling the actuators.

FIG. 7 illustrates different feedback loops for the control of pressure applied by the pads of the physical therapy tool. These feedback loops may condition the pressure within the tool (e.g., within the actuators) so that the pressure profile within an actuator may be regulated, allowing the actuator to have a pressure that is continuously varying. Feedback may be used to control pressure within an actuator because the controller can adjust the pressure from the pressure within the actuator to account for pressure from the pressure source, pressure applied by the practitioner, and pressure from the subject's back. Thus, an actuator may follow a controller pressure profile because the controller receives feedback from one or more feedback loops.

The controller may include one or more closed-loop systems that operate on different time scales, and that connect with different components of the tool. For example, an outer loop (not shown) may include the practitioner, the tool and the subject. Or, more specifically, the outer loop consists of the practitioner, the tool and an adjacent pair of the subject's vertebrae. An inner (or fast loop) may control the pressure regulator. The pressure regulator (e.g., a VY-1100 pressure regulator 725, as shown in FIG. 7) may contain an internal pressure sensor and have a closed-loop feedback system that maintains a set or selected pressure. The controller may use another feedback loop to assist the regulator in following a pressure profile. For example, a pressure profile may be selected from profiles (e.g., digitally stored within a memory) or input, e.g., via a keyboard, button or other input. The controller may instruct the pressure regulator 725 to follow the pressure profile. For example, the controller may convert a digital profile into a proportional voltage that is provided to the pressure regulator. The pressure regulator may respond to the proportional input to supply the desired pressure to an actuator, and may include an internal pressure sensor that is part of a closed-loop feedback system to help maintain the input pressure.

Another feedback loop may incorporate a second pressure sensor that is external to the pressure regulator. This loop is sensitive to backpressure from the applicator pistons, and may detect errors in the pressure waveform and make corrections. This slower feedback loop may compensate for mechanical imperfections in the pressure regulator. The second loop may also be adaptive. Thus, the second loop may help account for the pressure applied by the practitioner, who is applying the tool against a subject's back with some pressure. Differences in a practitioner's application technique may result in differences in backpressure. Thus the controller may adapt to the effect of pressure applied by the practitioner.

Operation of the Tool

In operation, the tool may be used to apply continuously varying pressure to each actuator so that the pressure within each actuator increases and decreases at a controlled rate. Thus, the tool is different from other physical therapy tools that cannot controllably apply a continuously varying pressure within an actuator, and instead only apply pulses of constant pressure (e.g., percussive "blows"). The continuously varying pressure is reflected in the pressure profile within different applicators during operation of the tool. The continuously varying pressure results in a tool that feels quite different to the subject and the practitioner operating the tool.

Figure 8A:
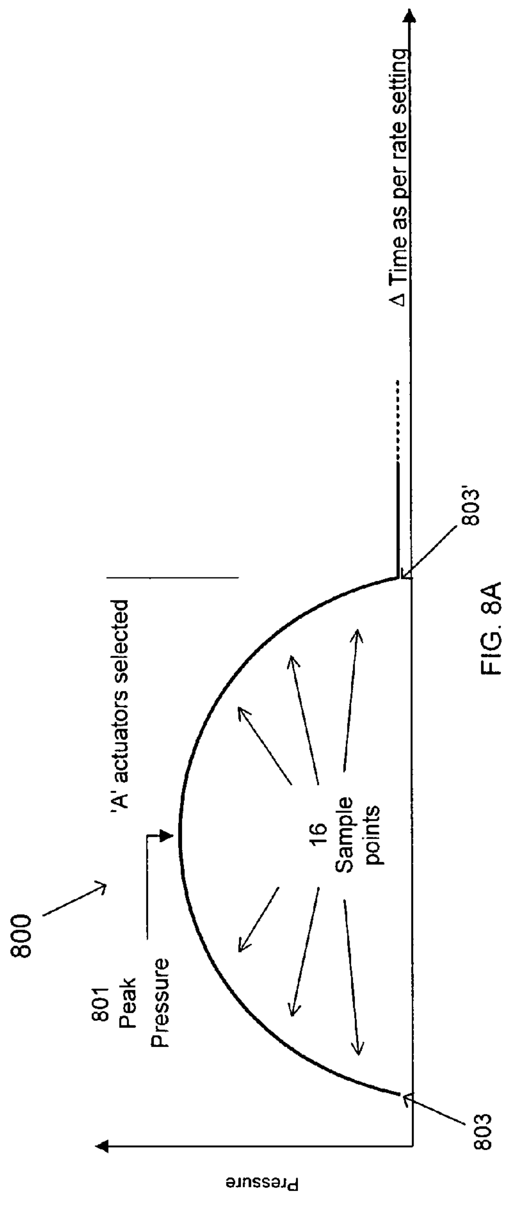
FIGS. 8A and 8B show one variation of a continuously varying pressure profile.
Figure 8B:
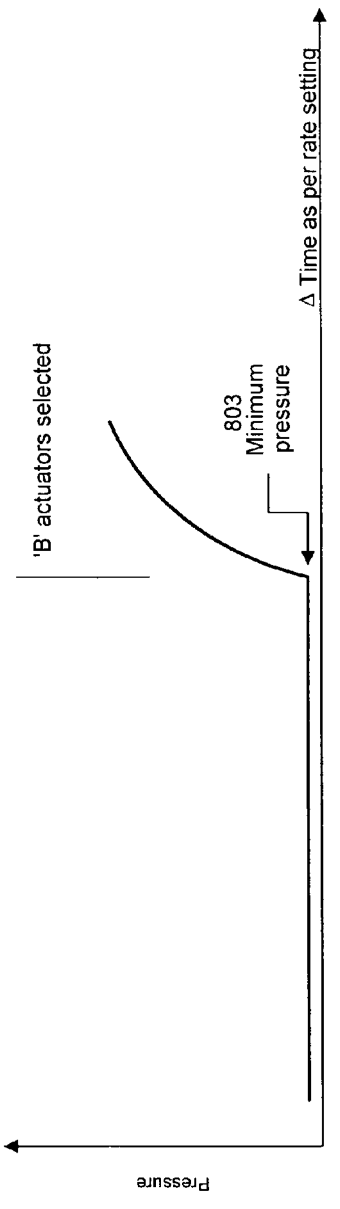

FIGS. 8A and 8B illustrate variations of pressure profiles having a continuously varying pressure. FIG. 8A shows the pressure profile that may be followed by the "A" pads. The pressure (on the Y axis) varies continuously over time (on the X axis) in a semi-circular arc. The "A" pads correspond to the applicators over the "A" positions in FIG. 1A when placed on a subject's back. FIG. 8B shows a portion of the pressure profile that may be followed by the "B" pads. This pressure profile is typical of a continuously varying pressure mode. As described, pads may be operated in opposable pairs or as individual pads.

A controller can coordinate pairs of pads to follow the pressure profiles shown in FIGS. 8A and 8B so that the pads may apply pressure reciprocally to a subject's back. The pressure within the actuator (or actuators) controlling the "A" pads rise along a continuous curve from a minimum pressure 803 to a peak pressure 801, before decreasing continuously along a curve back to a minimum pressure 803'. The minimum pressure may correspond to the pressure at which the pad retracts. Thus, the controller regulates the pressure within the actuator(s) controlling the "A" pair of pads so that the pressure within the actuator(s) follows the semi-circular curve shown. As described above, the controller may include one or more feedback loops to assist the controller in accurately tracking this pressure profile. In some variations, the "B" pads track the pressure profile shown in FIG. 8B, shown on the same time axis as FIG. 8A. Thus, the actuator(s) connected to the "B" pads follows a similar continuous curve, which is offset in time from the "A" pads. The pressure profiles in FIGS. 8A and 8B may be cyclically repeated so that the pressure within the actuators controllably increases and decreases along the continuous curve during part of the cycle, and is kept below the minimum pressure over part of the cycle. The entire cycle is repeated after some pressure cycle time. The portion of the cycle during which the pressure is below the minimum pressure threshold may be referred to as the dwell time. These pressure profiles may be the "target" pressure applied to the actuators, or they may be the actual pressure in the actuators being controlled.

The controller may receive inputs to alter the shape of the pressure profile, including the timing of the entire pressure profile cycle or other aspects of the pressure profile. For example, the controller may include inputs (e.g., user inputs) to alter cycle duration, peak pressure, dwell time, or combinations thereof, for the pressure profile. In some variations, the inputs may be selected from a range or menu of inputs. For example, a user may select a peak pressure from within a range. The actual pressure within the actuator will depend upon the pressure supplied (e.g., psi) and the volume the actuator (e.g., the actuator cylinder). Since the actuator volume is typically a constant, the pressure supplied can be referred to as the actuator pressure (in psi). For example, FIG. 9 shows a look-up tape of peak pressures corresponding to user-selectable "efforts" for a continuously varying pressure mode. Thus, the user may select the desired "effort" for the tool to exert during the pressure profile from a relative range of 1 to 9. The controller may then reference the look-up table to determine what peak pressure this corresponds to for the current (e.g., continuously varying pressure) mode. The look-up table in FIG. 9 shows peak pressures corresponding to relative "efforts" for a continuously varying pressure profile.

FIG. 9 also indicates a look-up table for the pressure cycle time (e.g., the cycle duration) in this mode. Thus, the user may select a relative "rate," and the controller may use a look-up table similar to the one shown in FIG. 9 to determine the pressure cycle time. Different modes may be selected having different peak pressures and pressure cycle times, as described below.

FIGS. 8A, 8B and 9 illustrate one variation of a continuously varying pressure profile for an actuator, having a semi-circular profile. The physical therapy tools described herein generally apply at least one type of continuously varying pressure profile, including profiles having a semicircular region, a curved region, a sloped region, a sinusoidal region, or the like. Thus the pressure applied by the pads of the actuator to the subject's back may be controlled so that pressure is increased and decreased in a manner that closely approximates the way a practitioner would use his or her hands to apply pressure. However, because the pressure applied by the pads is typically proportional to the pressure applied to the actuators, the practitioner does not have to use his or her fingers to apply pressure. Instead, the practitioner holds the tool (e.g., the applicator) against the subject's back, and may guide the tool up and down along the subject's spine by applying light pressure to move the tool as described above. The tool may therefore be balanced so that light pressure in the direction of motion will guide the tool over the subject's back.

The tool may also switch between modes. The mode of the tool may refer to the pressure profile to be applied to the actuators by the controller. Thus, in some variations, the mode may be a continuously varying pressure mode. Other modes include step-pulse high frequency mode and step-pulse low frequency mode. Any appropriate mode (e.g., any appropriate pressure profile) may be used. In operation, the tool may be switched between modes, and parameters within the modes may be user selected or automatically selected by the tool.

A. Continuously Varying Pressure Mode

As described above, the physical therapy tools descried herein generally include a continuously varying pressure mode. This mode may also be referred to as a manipulation mode (because it may be used to manipulate opposite pairs of vertebra), as shown in FIG. 1. In this mode the diagonally opposed actuator (piston) pairs are operated reciprocally (in turn), as shown in FIGS. 8A and 8B. The actuator pairs are provided with a controlled pressure during the cycle, according to a specific pressure profile. Application of pressure by the applicator from the pairs of pads may be manually controlled by the practitioner by pressing the applicator (handset) against the subject's back. The tool may deliver a smooth cyclic pressure that may be useful to adjacent transverse processes of the spine. Since the practitioner has to press down on the applicator to deliver the treatment, the pressure that is actually delivered to the subject's back is controlled/modified by the downward force supplied by the practitioner's hands.

Within the continuously varying pressure mode, the duration of the pressure cycle of the actuators may be selected by the user (rate setting), as previously described. Likewise, the peak value of the pressure fed to the actuators may be user selectable (e.g., effort setting). For example, user selectable settings may be entered by up/down buttons on the console (see FIG. 2), and the console may also include a display (e.g., an LED display) indicating the relative setting. In one variation, the selected rate and effort values (e.g., 1 to 9) are displayed on color-coded 7 segment LED displays. In some variations, the actual pressure supplied to the actuator volumes or time values (e.g., in psi and milliseconds) may be displayed.

The range of values used in this mode may be stored in a look-up table, such as the table shown in FIG. 9. Look-up tables may be incorporated into software, hardware, or some combination thereof, and may be included as part of the controller. In some variations, a look-up table is included as part of a memory.

The controller may coordinate the pressure profile in the actuators so that the delivery of the pressure profile by the actuator is smooth. In particular, the tool may include miniature valves (e.g., solenoid valves) that may operate at very low supply pressures. The electronic pressure regulator may therefore respond quickly, and can output very low pressures. As previously described, an electronic pressure sensor may be included as part of the output of the regulator to assist in feedback to the controller. The control electronics may measure the actual pressure delivered, and form a closed-loop control system that modifies the input to the pressure regulator to achieve tight control of the actual pressure curve. This feedback control may be particularly important at the extreme operating settings (e.g., a minimum pressure & maximum speed).

The tool may also include more than one manner of venting (or controlling venting) to release pressure from the actuators or other parts of the system, allowing the actuators to follow the desired pressure profiles. In general, the change-over point in the pressure profile curves (e.g., the point of minimum pressure 803) is a critical area for the smoothness of the delivery, since the pressure is at a minimum, and air flow is sluggish and mechanical friction effects may be magnified. Thus, the air pressure must be properly vented so that even at very low air pressures the actuators can follow the desired pressure profile. The tool may therefore include vents for venting from the applicator (e.g., from the actuator out through a valve in the applicator) as well as venting through the pressure supply line (e.g., back through the line supplying air to the actuator).

In some variations, the actual time that the changeover point occurs (e.g., switching between extended pads) may be modified based on the actual pressure within the actuators, to prevent a sudden change in the direction of force from the applicators which may result in a small but detrimental impact effect on the subject's back. For example, the actual pressure within an actuator may be monitored so that changeover occurs when the pressure actually reaches a predetermined optimal value (e.g., near or at some minimum value). The actual pressure within the system is dynamically dependent upon the practitioner and the subject, since the practitioner is applying the tool against the subject's back and the subject's back is effectively "pushing back" against the tool. The response of the actuator position in response to these pressures may change the volume of the system (pushing against the actuator) which affects the pressure, which in turn is adjusted by the system.

Using a smooth (e.g., regular curve) may also enhance the smoothness of the pressure delivered by the tool. For example, a hemispherical pressure profile curve may maximize the work done on each cycle. Furthermore, the closed-loop feedback system described herein (including the pressure sensor) may be used by other portions of the controller. For example, the controller may monitor the pressure at various nodes in the tool for failsafe purposes. Thus, the controller may include an automatic shutdown feature if the tool (e.g., the pressure in a portion of the tool) exceeds some permitted or pre-determined parameters. In some variations, the automatic shutdown feature is not triggered unless errors (e.g., which occur when the pressure exceeds a permitted value) are flagged on some number of consecutive pressure cycles.

Figure 10:
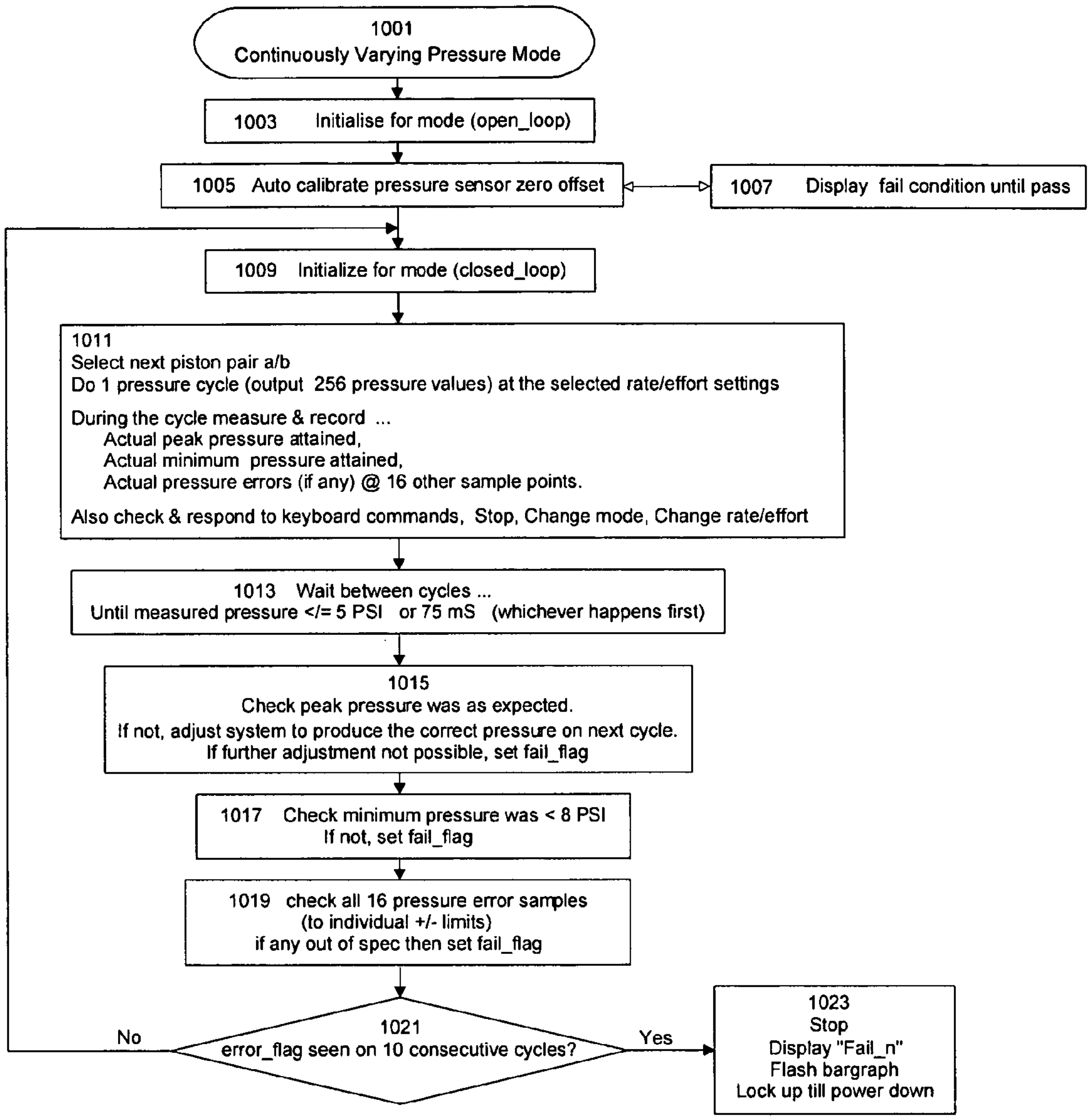
FIG. 10 illustrates one variation of the continuously varying pressure mode logic, as described herein.

The controller may include control logic (e.g., continuously varying pressure mode logic) for controlling and monitoring the pressure when the tool is operating in the continuously varying pressure mode. For example, FIG. 10 illustrates a flowchart showing continuously varying pressure mode logic that determines if the tool actuators are correctly following the target continuous pressure profile. This logic instructs the controller to monitor various parameters from the actuators as the tool follows a continuous pressure profile. If any of the parameters are not within acceptable limits, the continuously varying pressure logic may adjust the pressure or may trigger a "failure," indicating that there is a problem with the tool.

In the example shown in FIG. 10, the continuously varying pressure mode is selected 1001, and the controller initializes the tool 1003 and calibrates the pressure sensor or sensors monitoring back pressure from the applicator 1005, 1007. At the start of a cycle (e.g., at the start of the pressure profile), the controller selects which actuators it will actuate (or which pair of actuators for the case of reciprocally actuating pairs) 1009, and begins the pressure profile by applying pressure 1011. During the application of the pressure profile, the controller may divide the cycle into discrete time periods (e.g., 256) that each have a target pressure consistent with the pressure profile. As previously described, one or more feedback loops (not shown) may assist the controller in maintaining the pressure within an actuator and achieving the desired target pressure by controlling the amount of pressure supplied to the actuator or released from the actuator over the time period. The controller may record the peak pressure reached during the cycle, and the minimum pressure attained 1011. The controller may also sample the actual pressure profile within an actuator at any point, and determine the error from the actual and target pressure profiles. User commands (e.g., a stop command, changes in modes, changes in the rate/effort of the pressure profile, etc.) may also be monitored 1011. After completing a cycle, the controller may wait 1013 for the pressure within an actuator to reach the minimum value (e.g., $\leqq$5 psi) or until some maximum waiting period (e.g., 75 ms), to help achieve a smooth transition between cycles of different actuators, as described above.

At the end of the cycle, the actual pressure values achieved may be compared and (if possible) corrected before the next cycle. For example, the peak pressure may be adjusted by comparing the actual peak pressure to the expected peak pressure 1015. If the peak pressure is not within an acceptable range (e.g., ±5 psi), then the controller may calculate a scalar (e.g., a scaling factor) with which to adjust the pressure supplied in the next cycle. If further adjustment is not possible, an error flag may be triggered. Similarly, the minimum pressure may also be compared with a preset minimum value (e.g., <8 psi), and an error flag may also be triggered if the minimum pressure of the actuator(s) does not fall below this value 1017. The shape of the actual pressure profile may also be compared to the ideal pressure profile. For example, individual points taken from the actual pressure profile may be compared to the target pressure at selected time points. If any of the actual pressures do not fall within some acceptable range, then an error flag may be triggered 1019. Finally, the controller may determine how many error flags were triggered (either during a single cycle, between consecutive cycles, or both) and if the number of error flags exceeds some value, it may trigger a failure of the tool, and possibly a power down, or it may otherwise indicate an error message 1023.

The tool may also include modes that are not continuous, such as step-pulsed modes.

B. Step-Pulse High Frequency Mode

Figure 11:
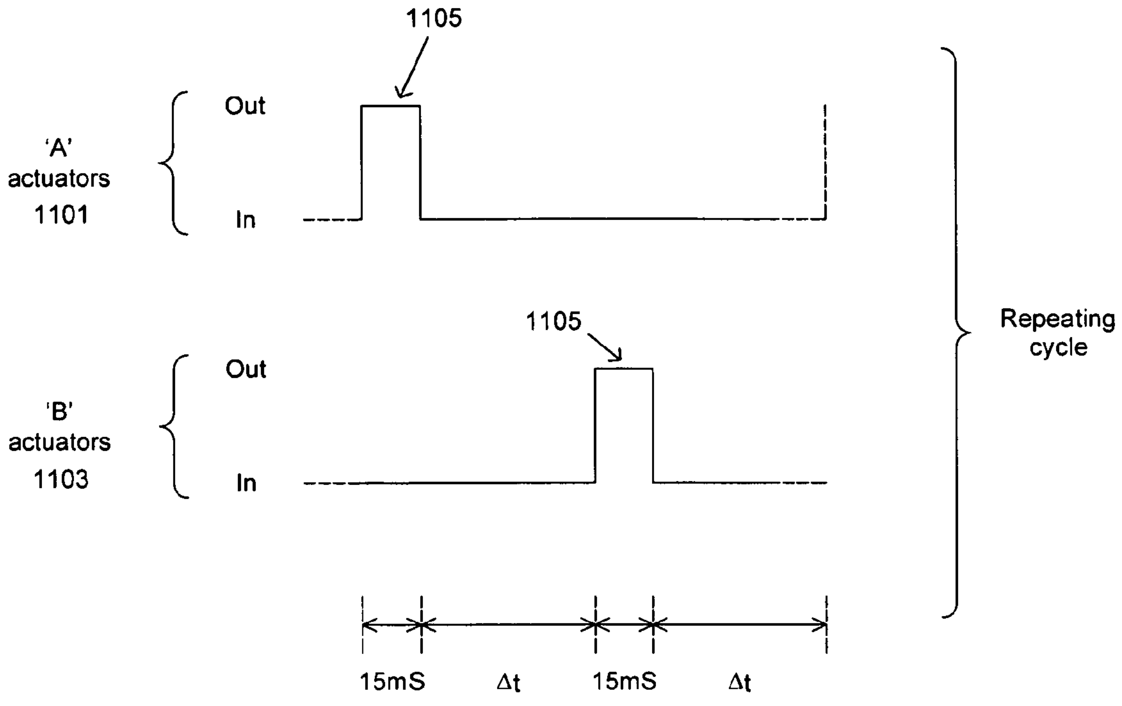
FIG. 11 shows one variation of a step-pulse high frequency pressure profile, as described herein.

The physical therapy tool may include a step-pulse high frequency mode, which may also be referred to as a spasm mode or an introductory mode. During the step-pulse high frequency mode, the actuators are rapidly extended for a short duration, which may provide an impact on the subject's back. The pressure profile for each actuator typically includes a pressure step, in which the ideal pressure profile is a square waveform, as indicated in FIG. 11. In FIG. 11, the upper trace 1101 shows the pressure profile for the actuator or actuators connected to a pair of pads, such as the "A" pads described above in FIG. 1. The lower trace 1103 shows the pressure profile for the actuator or actuators connected to another set of pads, such as the "B" pads.

Thus, in the step-pulse high frequency mode, actuators connected to one or more pads transition from a low pressure (e.g., a minimum pressure) state to a high pressure state that is approximately constant for some duration, during which the actuator may be extended (e.g., the pad is "out" or extended) 1105. The transition from the low pressure state to a high pressure state for the step-pulse does not have to be instantaneous. In some variations, the actuator is held at the maximum pressure (the step) for approximately 15 ms during the step-pulse high frequency mode. Thus the duration of the peak is approximately 15 ms. The peak pressure within the actuator is typically a constant pressure to which the step raises. In some variations, this peak pressure is selected by a user (e.g., as described before for the continuously varying pressure mode), or is preset by the controller. For example, the pressure may be a value selected from the range including about 10 to about 30 psi. In some variations, the pressure is approximately 15 psi, 18 psi, 21 psi, or 25 psi for the peak value of the step-pulse high frequency mode.

The step-pulse high frequency mode may also include a dwell time ($\Delta t$) during which the actuators are all at a minimum pressure value (e.g., when the pads connected to the actuators are "in" or retracted). For example, this dwell time may be selected from within the range of about 10 ms to about 60 ms. In some variations, the dwell time is approximately 15 ms, 20 ms, 25 ms, 30 ms, 35 ms, 40 ms, 45 ms, 50 ms, or 55 ms. Thus, the cycle time or cycle duration (the time over which the step-pulse cycle repeats) may be the combination of the dwell times and the step durations. In some variations, there is a different dwell time between different actuators. The step-pulse high frequency mode may also include a reciprocating pulse interval that indicates the time lag between the start of the pressure profile cycle for the first (e.g., the "A") actuator or actuators and the start of the pressure profile cycle for the second (e.g., the "B") actuator or actuators. In some variations, the reciprocating pulse interval is approximately half of the cycle duration.

As described above, the controller may receive inputs that select or alter parameters of the pressure profile for the step-pulse high frequency mode. For example, the controller may include inputs (e.g., user inputs) to alter cycle duration, peak pressure, dwell time, or combinations thereof. In some variations, the inputs may be selected from a range or menu of inputs. For example, a user may select a peak pressure from within a range. As described above, the actual pressure within the actuator is a function of the geometry of the actuator and the pressure supplied. FIG. 12 shows a look-up table of peak pressures corresponding to user-selectable "efforts." In this table, the peak pressure corresponds to the pressure supplied to the actuator in psi. Thus, the user may select a desired "effort" (e.g., maximum pressure for the step-pulse) for the pressure profile from a relative range of 1 to 9. The controller may then use the look-up table to determine what peak pressure this relative value corresponds to for the current step-pulse high frequency mode. The look-up table of FIG. 12 also indicates different dwell times (and therefore the cycle durations) between pressure step pulses corresponding to different relative values. Thus, a user can select a relative rate (dwell time), and the controller may use the look-up table to determine the dwell time for the pressure cycle.

Figure 13:
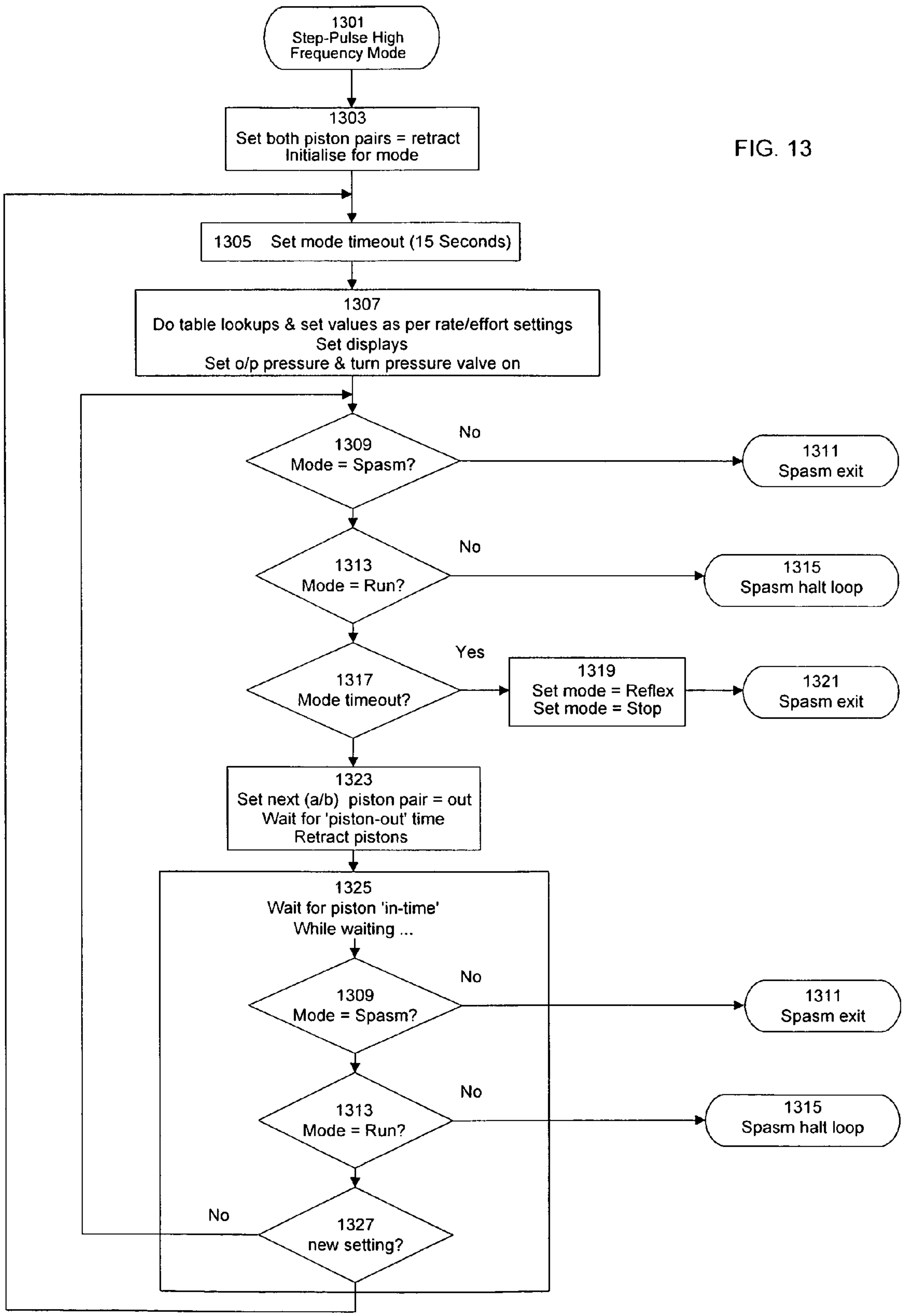
FIG. 13 illustrates one variation of the step-pulse high frequency mode logic, as described herein.

The physical therapy device described herein may also include step-pulse high frequency mode logic. The controller may execute the step-pulse high frequency mode logic to apply the step-pulse high frequency mode to the actuators. FIG. 13 shows one variation of step-pulse high frequency mode logic in which two sets of pads connected to at least two actuators are cyclically driven by high-frequency step-pulse pressure profiles, as shown in FIG. 11. In FIG. 13, the step-pulse high frequency mode is selected 1301, and the actuators are initialized 1303. In some variations, this means that all of the actuators are retracted 1303. The step-pulse high frequency mode may include a user adjustable or non-adjustable auto-timeout feature to limit the amount of time that the tool stays in the step-pulse high frequency mode. For example, when a practitioner selects the step-pulse high frequency mode, and presses "run," a timer may limit the amount of time spent in this mode to 15 seconds (for example), after which the unit stops and switches to another mode. In FIG. 13, this is indicated by the "mode timeout" 1305. In this variation, the mode timeout is a timer that counts down from 15 seconds. Any of the modes described herein may include similar auto timeout features that automatically switch between modes (or switch the device off) after some amount of time has passed. The amount of time can be user selected or input, or it can be preset and not user adjustable.

The step-pulse high frequency mode logic may refer to a look-up table, such as the look-up table of FIG. 12, to determine what the cycle duration, peak pressure, or dwell time may be, based on either pre-set or user-selected choices 1307. For example, in some variations, a user may select a relative value representing the effort or peak pressure applied to an actuator. The relative value may be a value of 1 to 9. The user may also select a relative dwell time from relative values of 1 to 9. These relative values may be used to reference a look-up table of actual pressures and dwell times. Thus, the physical therapy tool may include an input (e.g., a keypad, key, button, dial, switch, etc.) for selecting the relative values. Further, the tool may include a display for displaying the relative values, or their corresponding actual values.

Once the parameters of the pressure profile have been defined, the pressure supply is primed 1307 so that it may be applied to an actuator by setting the supply to provide the peak pressure. The step-pulse high frequency mode logic may continuously monitor user inputs that may change the mode 1309, 1311, the operation (e.g., run/stop) 1313, 1315, and any time limits (e.g., the mode timeout) 1319, 1321. Once the step-pulse high frequency mode logic selects which actuators it is going to actuate (e.g., the "A" actuators or the "B" actuators) 1323, the actuators are activated to a peak pressure for a duration of the pulse (e.g., an "out" or extended duration such as 15 ms) 1323. The step-pulse high frequency mode logic then retracts the actuators 1323, and may toggle the controller to select the next set of actuators to be extended (e.g., the "B" actuators) as part of the cycle. The step-pulse high frequency mode logic may then wait for a period equivalent to the dwell time before actuating the other set of actuators. While waiting, the step-pulse high frequency mode logic may monitor the mode 1309, 1311, the operation (e.g., run/stop) 1313, 1315, and any new settings 1327.

Thus, the step-pulse high frequency mode may apply step-pulses of pressure to reciprocating pairs of pads. The reciprocating pairs of pads generally correspond to diagonally opposed actuator pairs (e.g., "A" and "B" pairs) that are operated in turn. Thus, the step-pulse high frequency mode may be used in combination with other modes, including the continuously varying pressure mode, and a step-pulse low frequency mode.

C. Step-Pulse Low Frequency Mode

Figure 14:
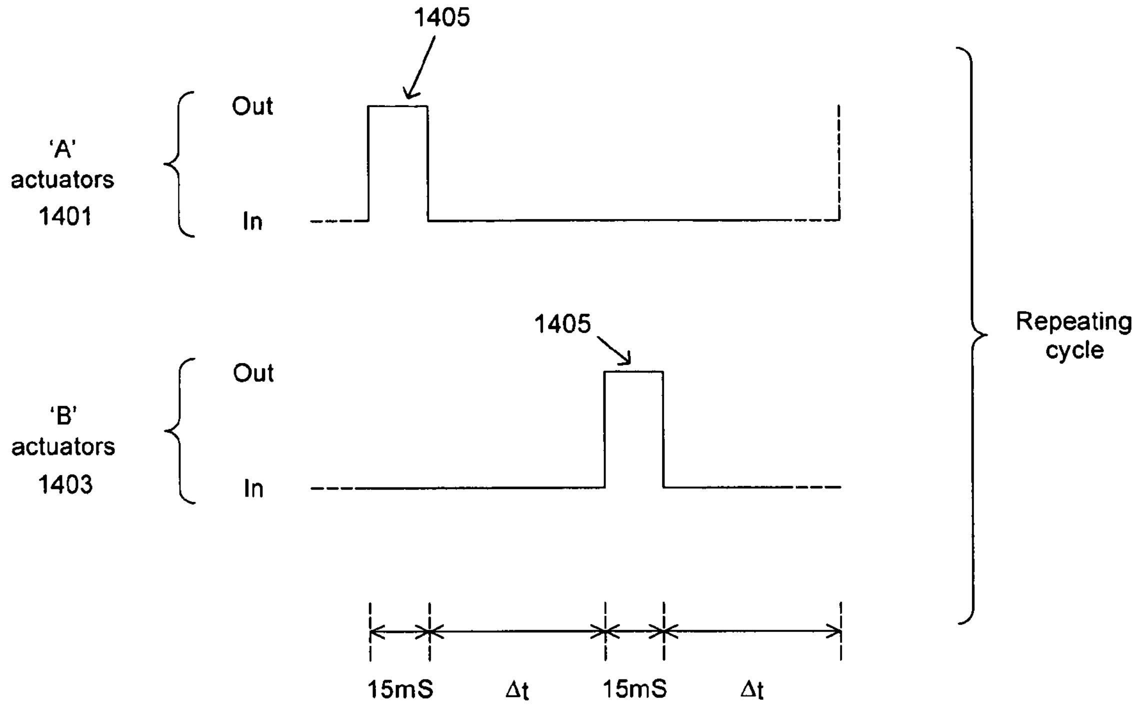
FIG. 14 shows one variation of a step-pulse low frequency pressure profile, as described herein.

The physical therapy tool may also include a step-pulse low frequency mode, which may be referred to as a reflex mode or a recovery mode. During the step-pulse low frequency mode, the actuators are extended for a short duration, which may provide an impact (e.g., "blow") on the subject's back. The cycle duration of the step-pulse low frequency mode is typically larger than the cycle duration of the step-pulse high frequency mode, but the two modes may be otherwise quite similar. For example, the pressure profile for each actuator typically comprises a pressure step, in which the ideal pressure profile is a square waveform, as indicated in FIG. 14. In FIG. 14, the upper trace 1401 shows the pressure profile for the actuator or actuators connected to one pair of pads, such as the "A" pads described above in FIG. 1. The lower trace 1403 shows the pressure profile for the actuator or actuators connected to another set of pads, such as the "B" pads.

In the step-pulse low frequency mode, actuators connected to one or more pads transition from a low pressure (e.g., a minimum pressure) state to a high pressure state that is approximately constant for some duration, during which the actuator may be extended (e.g., the pad is "out" or extended) 1405. The transition from the low pressure state to a high pressure state for the step-pulse does not have to be instantaneous. In some variations of the step-pulse low frequency mode, the actuator is held at the maximum pressure (the step) for approximately 15 ms. Thus, the duration of the peak is approximately 15 ms. The peak pressure within the actuator is typically a constant pressure to which the step rises. In some variations, this peak pressure is selected by a user (e.g., as described before for the step-pulse high frequency mode and the continuously varying pressure mode), or is preset by the controller. For example, the pressure may be a value selected from a range for the peak pressure of the step-pulse low frequency mode.

The dwell time of the step-pulse low frequency mode ($\Delta t$) is typically larger than the dwell time of the step-pulse high frequency mode. For example, the dwell time of the step-pulse low frequency mode may be selected from within the range of about 100 ms to about 1.6 sec. In some variations, the dwell time is approximately 100 ms, 290 ms, 480 ms, 660 ms, 850 ms, 1040 ms, 1230 ms, 1410 ms, or 1600 ms. Thus, the cycle time or cycle duration (the time over which the step-pulse cycle repeats) may be the combination of the dwell times and the step durations. In general, the cycle time for the step-pulse low frequency mode is larger than the cycle time for the step-pulse high frequency mode, as the names imply.

As described above, the controller may receive inputs that select or alter parameters of the pressure profile for the step-pulse low frequency mode. For example, the controller may include inputs (e.g., user inputs) to alter cycle duration, peak pressure, dwell time, or combinations thereof. In some variations, the inputs may be selected from a range or menu of inputs. For example, a user may select a peak pressure from within a range. FIG. 15 shows a look-up table of peak pressures corresponding to user-selectable "efforts." The actual pressure within the actuator is dependent upon the geometry of the actuator. Thus, the user may select a desired "effort" (pressure step) for the pressure profile from a relative range of 1 to 9. The controller may then reference the look-up table to determine what peak pressure this corresponds to for the current mode. As described for FIGS. 9 and 12, peak pressure in the table is shown in psi, corresponding to the pressure supplied to the actuators. The look-up table of FIG. 15 also includes different dwell times (and therefore cycle durations) between pressure step pulses corresponding to different relative values between 1 to 9. A user may select a relative rate (e.g., dwell time), and the controller can use a look-up table similar to the one shown in FIG. 15 to determine the pressure cycle dwell time.

Figure 16:
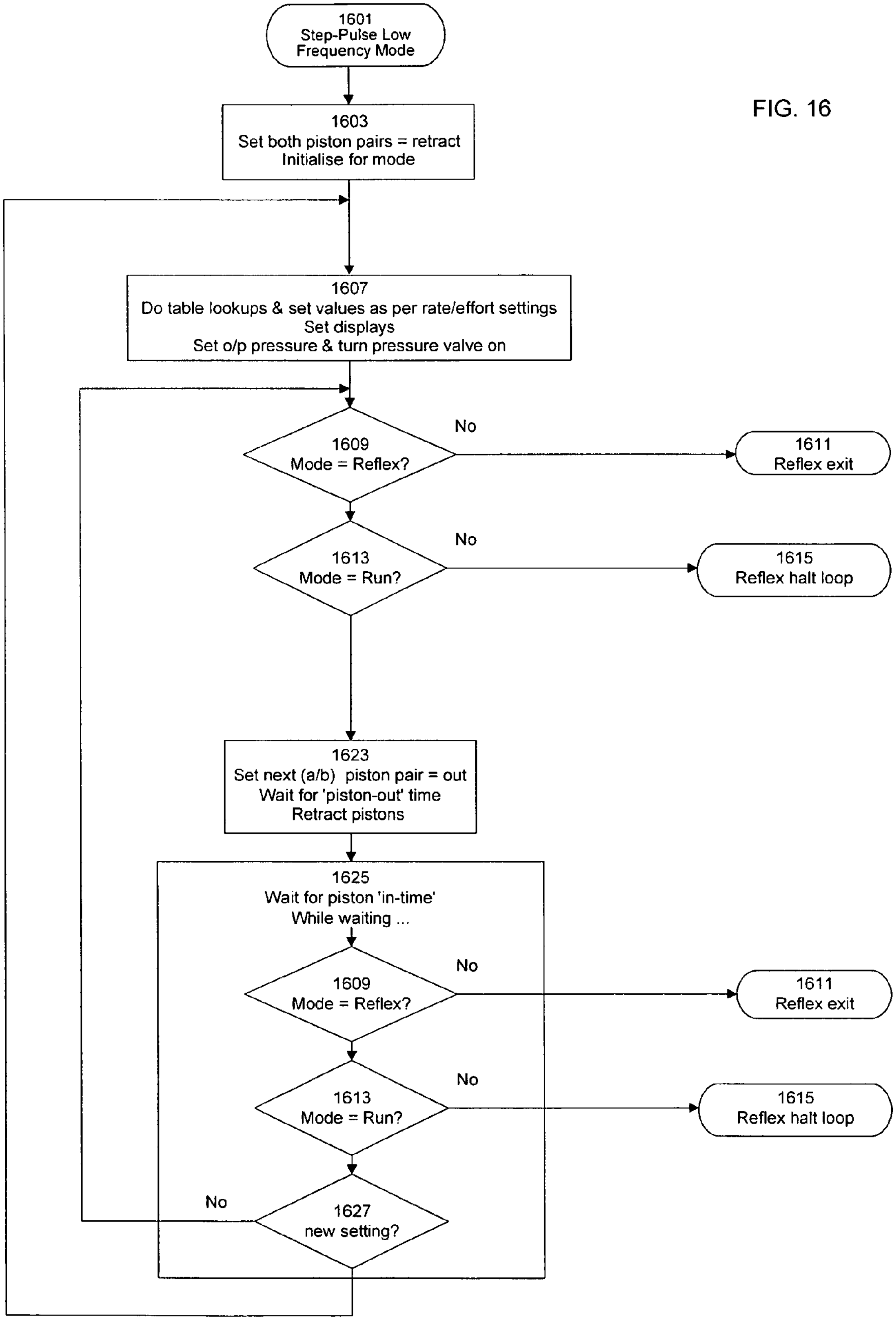
FIG. 16 illustrates one variation of the step-pulse low frequency mode logic, as described herein.

The physical therapy device may also include step-pulse low frequency mode logic. The controller may execute the step-pulse low frequency mode logic to apply the step-pulse low frequency mode to the actuators. FIG. 16 shows one variation of step-pulse low frequency mode logic in which two sets of pads connected to at least two actuators are cyclically driven by low frequency step pulse pressure profiles, as shown in FIG. 14. In FIG. 16, the step-pulse low frequency mode is selected 1601, and the actuators are initialized 1603. In some variations, this means that all of the actuators are retracted 1603.

The step-pulse low frequency mode logic may then refer to a look-up table, such as the look-up table of FIG. 15, to determine what the cycle duration, peak pressure, or dwell time may be, based on either pre-set or user-selected choices 1607. For example, in some variations, a user may select a relative value representing the effort or peak pressure applied to an actuator. The relative value may be a value of 1 to 9. The user may also select a relative dwell time from a values of 1 to 9. These relative values may be used to reference a look-up table of actual pressures and dwell times. Thus, the physical therapy tool may include an input (e.g., a keypad) for selecting the relative values. Further, the tool may include a display for displaying the relative values, or their corresponding actual values.

Once the parameters of the pressure profile have been defined, the pressure supply may be primed 1607 to apply the peak pressure to an actuator. The step-pulse low frequency mode logic may also continuously monitor user inputs that may change the mode 1609, 1611 or the operation (e.g., run/stop) 1613, 1615. Once the step-pulse low frequency mode logic selects which actuators it is going to actuate (e.g., the "A" actuators or the "B" actuators) 1623, the actuators are activated by the peak pressure for a duration of the pulse (e.g., an "out" or extended duration such as 15 ms) 1623. The step-pulse high frequency mode logic then retracts the actuators 1623, and may toggle the controller to select the next set of actuators to be extended (e.g., the "B" actuators) as part of the cycle. The step-pulse high frequency mode logic may then wait for a period equivalent to the dwell time before actuating the other set actuators. While waiting, the step-pulse high frequency mode logic may monitor the mode 1609, 1611 and the operation inputs (e.g., run/stop, mode, etc.) 1613, 1615.

The step-pulse low frequency mode may apply step-pulses of pressure to reciprocating pairs of pads. In some variations, the reciprocating pairs correspond to diagonally opposed actuator pairs (e.g., "A" and "B" pairs) that are operated in turn. Thus, the step-pulse low frequency mode may be used in combination with other modes, as described above.

In general, the tool may be operated to follow any appropriate mode, or combination of modes. In some variations, the tool includes pre-programmed modes (e.g., continuously varying pressure modes, step-pulse low frequency modes, step-pulse high frequency modes, etc.). In some variations, the tool may be programmable, so that new or alternative modes may be used. As described above, the parameters (e.g., peak pressure, dwell duration, cycle duration, etc) may be selected for any mode. Although the examples provided above illustrate some variations of modes, other modes are possible, including modes coordinating the movement of individual pads, or modes where different actuators are actuated by different pressure profiles.

Physical Therapy Systems

A physical therapy system may include any of the physical therapy tools described herein, as well any appropriate additional component. For example, a physical therapy system for use in treating a spine may include a bench for supporting a subject. In some variations, the system includes a stand for supporting the physical therapy tool.

Figure 17:
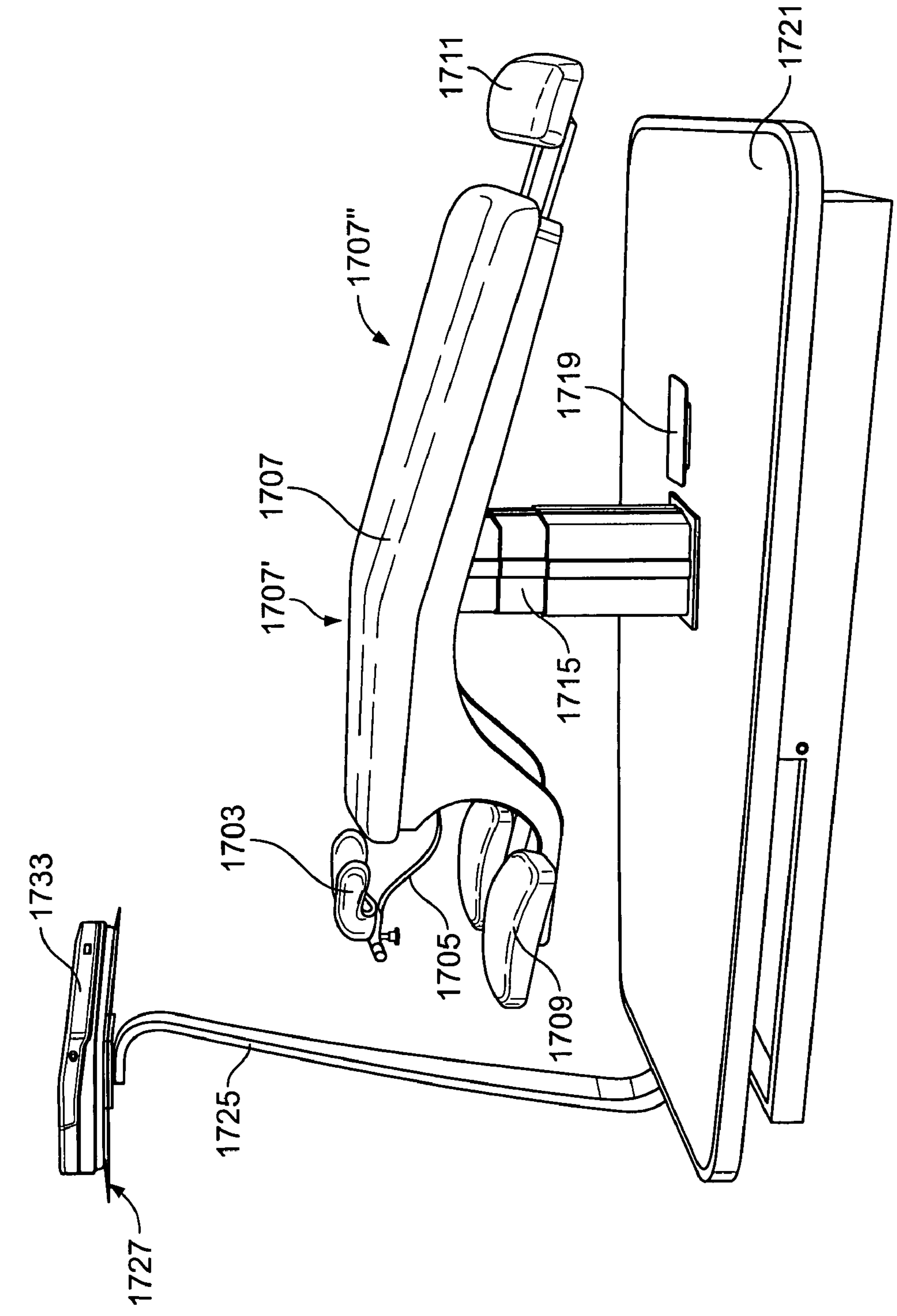
FIG. 17 shows one variation of a physical therapy bench, as described herein.

The system may include a portable treatment bench. For example, U.S. Pat. No. 6,532,609 to Taylor et al. describes one type of physical therapy bench that may be appropriate for use with the physical therapy tools described herein. This patent is herein incorporated by reference in its entirety. A bench may also be referred to as a table. The system may include a treatment bench that is or is not portable. Another type of physical therapy bench that may be used is illustrated in FIG. 17.

Any appropriate bench may be used. FIG. 17 shows a bench 1700 including a head support 1703, a body supporting region 1707, arm rests 1709, and lower leg rest 1711. The height of the bench shown in FIG. 17 may be adjusted. This bench includes a platform 1721 and a positionable stand 1725 for holding a physical therapy tool. The stand may be moved to positions around the bench without interfering with the bench or with a practitioner standing on the platform around the bench. In general, a physical therapy bench may include any of the features described below and illustrated in FIG. 17.

The head support (head rest) 1703 is a floating head support that is connected to the rest of the bench by a spring-type connection, such as a leaf spring 1705. The spring connection may provide adjustable amounts of support. For example, the stiffness of the connection between the head support and the rest of the bench may be variable and/or adjustable, allowing the weight of the head to position the height of the head support relative to the rest of the bench. In some variations the head support includes one or more controls (e.g., knobs) for adjusting the stiffness. The distance of the head support from the rest of the bench may also be adjustable. For example, the head support may also include controls for adjusting its angle or distance from the rest of the bench.

The headrest may be padded, and may be of any appropriate shape, including U-shaped. In some variations, the headrest has two separate body-contact surfaces for contacting different sides of the subject's face, when the subject is laying face-down on the bench. The headrest may be shaped or oriented so as to approximately conform to the subject's head or face. The surfaces of the headrest that contact the subject may be washable, and may include a covering that can be removed. For example, the surface may be covered with a disposable sterile covering.

The body supporting region 1707 may support the bulk of the subject's body. In some variations, the body supporting region 1707 is curved so that the subject's torso may be supported at a different incline than the subject's lower body. The curve may be a gradual curve, or the curve may be a bend, as shown in FIG. 17. In the variation shown in FIG. 17, the body supporting region 1707 is divided into a torso supporting region 1707' and a lower body supporting region 1707". The torso supporting region 1707' and the lower body supporting region 1707" may be regions of a single piece (or tow or more integrally connected pieces), but each region may have different surface angles. The surface angle of the trunk region is typically more horizontal (e.g., more parallel with the ground) than the lower body supporting region. The lower body supporting region is typically angled so that the lower body (e.g., from the waist of the subject downwards) is less horizontal than the torso region when the subject is lying on the bench. The different angles may provide comfort to the subject and access to for the practitioner to reach the subject's back.

In some variations, the torso supporting region and the lower body supporting region are separate or separatable, and may be independently adjustable. For example, the surface angle (e.g., the angle of the body-contact surface of the bench with respect to horizontal) may be separately adjustable for each region.

Different parts of the body supporting region may have different widths or lengths. In this case, the width and length refers to the dimensions of the body contacting surface (e.g., the upper surface) of the body supporting region of the bench. The width is typically the shorter dimension and the length is typically the longer dimension. Thus, the torso supporting region may have a narrower width than the lower body supporting region. For example, the torso supporting region may be less than the average shoulder-width distance of a subject, so that the subject's arms are not supported by the bench. In some variations, the width of the body supporting region of the bench (particularly the width of the torso supporting region) is adjustable. In some variations, the upper portion of the torso supporting region (towards the head rest) is narrower than the lower portion of torso supporting region. In some variations, the width of the torso supporting region tapers as it approaches the head support.

The surface of the body supporting region may be washable or may be configured to be covered with a disposable sterile cover that can be changed between subjects. For example, the bench may include attachment sites, guides, channels, or the like for use with such a disposable cover. The surface of the body supporting region may also be padded. In some variations, the surface of the body-supporting region at least partly conforms to the shape of a subject lying thereupon.

The bench may also include arm rests 1709. The arm rests may be located beneath the level of the body supporting region 1707. In some variations, the height of the arm rests may be adjustable relative to the body support region. The angle or position of the arm rests may also be adjustable. Thus, a subject's arms may hang below the level of the bench, allowing the subject to lie recumbent on the bench face down, so that the subject's arms and shoulder blades are relaxed, further enhancing access to the spinal region.

The bench may also include a leg extension 1711. The leg extension is generally adjustably attached to the end of the bench opposite to the head rest, so that it may be extended or retracted to support the lower portion of a subject's legs when the subject is lying on the bench. The leg rest may include a lock, to lock the leg rest into position.

The bench height may be adjustable. For example, in some variations, the bench is supported by a single telescoping support 1715, as shown in FIG. 17. The telescoping support or column may be manually or electrically controlled. In FIG. 17, the telescoping support consists of three concentric rectangular tubes. The height of the bench may be raised or lowered by a control such as a foot petal 1719. The height control may be located anywhere on the bench, or remotely located. The bench may be supported on one support leg. For example, in FIG. 17, the telescoping support 1715 is centrally located, so that it is out of the way of the feet and legs of the practitioner using the bench to treat a subject.

The bench may be at least partly surrounded by a deck 1721. The deck provides a slightly elevated and flat surface for the practitioner to stand and work on, free from interfering cords and the like. Thus the deck 1721 may assist the practitioner in comfortably reaching the back of a subject lying on the bench. The deck may also hide and protect other components of the physical therapy system. For example, the deck may cover power cords, machinery and any support base (e.g., for the telescoping support). The deck may also be textured or coated to enhance the footing of the practitioner. In some variations, the deck may include an upper (standing) surface that is somewhat resilient, to enhance the comfort of the practitioner. For example, the standing surface may comprise a rubber material. The upper surface of the deck may also be removable or replaceable (e.g., for cleaning, etc.).

In some variations, the system may also include a stand 1725 for holding the physical therapy tool 1733. The stand may be an adjustable stand that can be adjustably positioned near the subject. The height of the stand may also be adjusted. In some variations, the horizontal distance from the subject may be adjusted. FIG. 17 shows a stand that is adjustable around the subject. The stand shown in FIG. 17 can swing around the bench so that it can be positioned on either the right side of the bench or the left side of the bench. This stand includes a single support 1725 that is attached to the bench beneath the deck. The stand may be positioned around the perimeter of the bench by applying pressure. In some variations, the stand includes a releasable lock to hold the bench in a set position. The stand may also include a flat surface 1727 for holding the physical therapy tool 1733. The physical therapy tool may be secured to the stand (e.g., by a lip, a cradle, screws, straps, etc.).

The physical therapy system may also include a power supply. For example, the system may include a power supply or adapter for converting wall voltage (line voltage) into power appropriate to support other portions of the system (e.g., the tool, bench, etc.). In some variations, the system includes a portable power supply, such as a battery power supply.

Methods of Use

The physical therapy tools described herein may be used to treat a subject's back. For example, a subject may first be examined by the practitioner to determine if treatment is advisable. The practitioner may use his or her experience to determine if the subject would benefit from application of the tool (e.g., to cause spinal joint mobilization). A subject in need of treatment may then be positioned so that the subject's back is accessible to the practitioner operating the tool. For example, the subject may be positioned on a table, plinth or bench, such as any of the adjustable benches described herein. Before applying the tool to the subject's back, a lubricant may be applied to either the tool, or the region of the subject's back to contact the tool, or both. Lubrication may prevent chafing by the tool, or friction in driving the tool, and may enhance subject comfort. Lubrication may also be applied to the back of the applicator (e.g., where the practitioner grips the applicator), or to the practitioner's hands.

In general, a physical therapy tool is placed against a subject's back and operated in any appropriate mode to apply cyclic pressure. A practitioner may apply pressure to hold the tool against the subject's back, and may move the tool along the back, over the subject's spine. In some variations, the tool is operated in at least a continuously varying pressure mode, as described above. For example, the tool is operated so that the actuators connected to two pairs of pads operate reciprocally to mobilize and/or manipulate a spinal joint and through contact and pressure on the surrounding paraspinal musculature, tissues, tendons, nerves and ligamentous structures also enhances paraspinal circulation, effects myofacial release, stimulates paraspinal muscle reflexes and re-educates neuromuscular kinesthetic posture and balance control. The pressure within each actuator, and therefore the pressure applied by the pads, is controlled by the tool so that it follows a continuously varying pressure profile. For example, each actuator may follow a cyclic, semicircular pressure curve having a peak pressure within a range (e.g., the pressure supplied to the actuator may be between about 20 psi to about 70 psi). The peak (or maximum) pressure of the pressure cycle may be user-selected or pre-set. Thus, the method may include selecting a mode. In some variations, the method includes selecting a mode parameter, such as the peak pressure, dwell time, and/or cycle duration. The practitioner may select mode parameters from a list or menu of parameters or reference values. For example, the pressure cycle duration (e.g., cycle time) may be selected for the continuously varying pressure mode using buttons on the console. Thus, the pressure cycle duration may be selected from a time between about 0.8 sec and 2.0 sec. In some variations, the pressure cycle duration is selected using buttons on the console of the tool.

The method of using the tool may also include a step of switching between a first mode (e.g., a continuously varying pressure mode), and a second, and/or third mode. For example, the second and/or third mode may correspond to a step-pulse high frequency mode or a step-pulse low frequency mode, as described above. In any mode, the practitioner may monitor the progress of the tool, and may guide the tool up and/or down the subject's back. The practitioner may hold the tool with a loose grip, and may choose to but is not required to apply a great deal of pressure to mobilize and/or manipulate the spinal joint.

The practitioner may apply a treatment protocol consisting of one or more modes of the tool. For example, one treatment protocol may include starting the treatment by applying the tool in the step-pulse high frequency mode (e.g., an "introductory" or "spasm" mode) for approximately 15 seconds, while running the applicator or the tool up and down the subject's back over the spine. Next, the tool may be switched to a continuously varying pressure mode (e.g., a "recovery" or "reflex" mode) and moved along the subject's back over the spine. The tool may be switched from the continuously varying pressure mode to a step-pulse low frequency mode (e.g., a "mobilization" mode) The step-pulse low frequency mode may mobilize spinal joints. Switching between the modes this way may progressively enhance the flexibility, mobility, elasticity and rebound of the spinal joints being treated. The practitioner may switch between these cyclic modes for as long as he or she feels appropriate. The practitioner may monitor the overall mobility of the spinal joints and may apply more or less treatment to different regions of the spine. At the end of a treatment period, the tool may be switched from the step-pulse low frequency mode into the step-pulse high frequency mode (e.g., for 15 sec), and finally switched off. At any point during treatment, the device may be switched off, or the mode may be manually adjusted or switched. For example, the peak pressure, cycle duration or dwell time may be adjusted for any particular mode. The treatment cycle may last as long or as short as desired. For example, the treatment cycle may last 30 min, 40 min., or longer or less.

The practitioner applying a treatment protocol may also choose to manually mobilize the sacrum, sacro-iliac, and coccygeal joints by applying one, two or all three modes of operation.

A treatment cycle may also be automatically controlled. For example, the tool may be pre-programmed to run a specific combination of modes for pre-defined times. The tools, systems and kits described herein may also be used to massage the back or to otherwise treat the back of any subject in need thereof.

Kits

The physical therapy tools described herein may comprise part of a kit. Kits for the use in treating a spine can also include lubricant for applying to the applicator of the tool, the subject's back, or the practitioner's hands. Kits may also include a bench (as described above), and instructions for use of any of the component parts of the kit.

Any appropriate lubricious material may be used as a lubricant. For example, the lubricant may be a cream, paste, spray or oil. The lubricant may be a water based lubricant or an oil based lubricant. The lubricant may include a grease. In some variations, the lubricant may comprise a coating on the pads of the tool. For example, the pads may include a lubricious surface, such as polytetrafluoroethylene (e.g., Teflon®), or other friction-reducing material.

Instructions may also be provided with a kit. The instructions may be written, electronic, pictographic, graphic, or audio. Instructions may include instructions about the use of any portion of the kit, including operation of the physical therapy tool, the physical therapy bench, or the entire system.

Although specific embodiments of the present invention have been illustrated in the accompanying drawings and described in the foregoing detailed description, it will be understood that the invention is not limited to the particular embodiments described herein, but is capable of numerous rearrangements, modifications, and substitutions without departing from the scope of the invention.

What is claimed is:

1. A physical therapy tool for use in treating a spine, comprising:

a plurality of actuators;

two pairs of pads, wherein each pad is connected to an actuator;

at least one variable pressure source; and a controller programmed and configured to vary the pressure supplied by the at least one variable pressure source to cyclically supply continuously varying pressure to each actuator to advance each actuator, wherein the pressure supplied by the pressure source to each actuator during advancement of that actuator increases continuously from a minimum pressure to a maximum pressure then decreases continuously from the maximum pressure to the minimum pressure.

2. The tool of claim 1, wherein the pads are spaced such that the tool can be applied to a subject's back so that the pads are positioned over two pairs of transverse processes on adjacent vertebra.

3. The tool of claim 1, wherein the tool is balanced such that the tool comprises a center of action so that the tool may be moved by applying light force at a center of push located apart from the center of action, resulting in a direction of travel extending in the direction from the center of push through the center of action.

4. The tool of claim 1, wherein the pads and the actuators are arranged as part of an applicator and the controller is arranged as part of a console.

5. The tool of claim 4, wherein the applicator is configured to be hand-held.

6. The tool of claim 1, wherein the actuators are pneumatically actuated.

7. The tool of claim 6, wherein the actuators vent through a port on the hand-held applicator and through a pressure supply line connected to the actuators.

8. The tool of claim 1, wherein the controller coordinates the two pairs of pads so that the two pairs of pads move reciprocally with respect to each other.

9. The tool of claim 1, further comprising a cycle duration input to select the duration of a pressure cycle of an actuator.

10. The tool of claim 1, further comprising a pressure input to select the peak pressure of a pressure cycle of an actuator.

11. The tool of claim 1, further comprising a dwell input to select the duration of a pressure cycle over which pressure is not applied to an actuator to extend a pad.

12. The tool of claim 1, further comprising a pressure sensor, wherein the pressure sensor detects back pressure from an actuator.

13. The tool of claim 1, further comprising a memory for storing a pressure profile of a cycle.

14. The tool of claim 1, further comprising mode logic for selecting a cycle pressure profile for the controller so that the controller may apply the cycle pressure profile to the actuators.

15. The tool of claim 14, wherein the mode logic receives user input to select between a step-pulse high frequency mode, a step-pulse low frequency mode, and a continuously varying pressure mode.

16. The tool of claim 14, wherein the mode logic receives user input to select the cycle duration, peak pressure applied, dwell time, or combinations thereof, for the pressure profile of a mode.

17. The tool of claim 14, wherein the mode logic automatically switches between modes after a predetermined time period.

18. A physical therapy tool for use in treating a spine, comprising:

two pairs of pads, wherein each pad is connected to a pneumatic actuator;

a solenoid valve configured to apply variable pressure to each pneumatic actuator; and a controller programmed and configured to control the solenoid valve to vary the pressure supplied by the solenoid valve so that the solenoid valve cyclically supplies a constantly varying pressure to each pneumatic actuator to advance each pneumatic actuator, wherein the pressure supplied by the pressure source to each pneumatic actuator during advancement of that pneumatic actuator increases continuously from a minimum pressure to a maximum pressure then decreases continuously from the maximum pressure to the minimum pressure.

19. The tool of claim 18, wherein the controller is configured to control the solenoid valve so that the pressure of each pneumatic actuator cyclically follows a curved pressure profile.

20. The tool of claim 18, wherein the controller is configured to control the solenoid valve so that the pressure of each pneumatic actuator cyclically follows a square pressure profile.

21. The tool of claim 18, further comprising mode logic for selecting a cycle pressure profile so that the controller may apply the cycle pressure profile to the actuators.

22. The tool of claim 21, wherein the mode logic selects between modes chosen from the group consisting of: a step-pulse high frequency mode, a step-pulse low frequency mode, and a continuously varying pressure mode.

23. A system for use in treating a spine, comprising:

a bench; and a physical therapy tool having at least two actuators; two pairs of pads, wherein each pad is connected to an actuator; at least one variable pressure source; and a controller programmed and configured to vary the pressure supplied by the at least one variable pressure source to cyclically supply continuously varying pressure to each actuator to advance each actuator, wherein the pressure supplied by the pressure source to each actuator during advancement of that actuator increases continuously from a minimum pressure to a maximum pressure then decreases continuously from the maximum pressure to the minimum pressure.

24. The system of claim 23, wherein the bench comprises a floating and bifurcated head support.

25. The system of claim 23, wherein the height of the bench is adjustable.

26. The system of claim 25, wherein the bench is supported by a telescoping support.

27. The system of claim 23, wherein the bench comprises arm rests.

28. The system of claim 23, wherein the bench comprises a leg extension.

29. The system of claim 23, wherein the adjustable bench has a curved body-supporting region so that a subject's torso may be supported at a different incline than the subject's lower body.

30. The system of claim 23, further comprising a deck at least partly surrounding the bench.

31. The system of claim 23, further comprising an adjustable stand for supporting at least part of the physical therapy tool, wherein the adjustable stand may be moved from one side of the bench to the other side of the bench.

32. A method of treating a subject's back, comprising:

placing a tool against the subject's back, the tool having at least one variable pressure source, at least two actuators and two pairs of pads, wherein each pad is connected to an actuator; and operating the tool in a first mode wherein the tool is programmed and configured to vary the pressure supplied by the at least one variable pressure source to cyclically supply a continuously varying pressure to each actuator to advance each actuator, wherein the pressure supplied by the pressure source to each actuator during advancement of that actuator increases continuously from a minimum pressure to a maximum pressure then decreases continuously from the maximum pressure to the minimum pressure.

33. The method of claim 32, wherein the step of operating the tool in the first mode comprises operating the tool so that the pressure profile of any of the actuators rises and falls in a semicircular curve.

34. The method of claim 32, wherein the first mode has a pressure cycle time of between about 0.8 sec and about 2.0 sec.

35. The method of claim 32, further comprising the step of operating the tool in a second mode, wherein each actuator is cyclically actuated by a step increase in pressure.

36. The method of claim 35, wherein the second mode maintains the peak pressure for about 15 ms of a pressure cycle time between about 100 ms and about 1.6 sec.

37. The method of claim 35, further comprising the step of switching between the first mode and the second mode.

38. The method of claim 32, further comprising moving the tool along the subject's spine.

39. The method of claim 32, further comprising:

operating the tool in a third mode so that each actuator is cyclically activated by a step increase in pressure, wherein the third mode maintains a peak pressure for a duration of about 15 ms of a pressure cycle time of between about 15 ms and about 55 ms.

40. The method of claim 32, comprising the step of applying a lubricant to the subject's back.

41. A method of treating a subject's back comprising:

placing a tool against the subject's back, the tool having:

at least one variable pressure source; two pairs of pads, wherein each pad is connected to an actuator;

operating the tool in step-pulse high frequency mode so that each actuator is cyclically activated by a step increase in pressure, wherein the step-pulse high frequency mode maintains a peak pressure for a duration of about 15 ms of a pressure cycle time of between about 15 ms and about 55 ms;

switching from the step-pulse high frequency mode to a step-pulse low frequency mode so that each actuator is cyclically activated by a step increase in pressure, wherein the step-pulse low frequency mode maintains a peak pressure for a duration of about 15 ms of a pressure cycle time of between about 100 ms and about 1.6 sec; and switching from the step-pulse low frequency mode to a continuously varying pressure mode wherein the tool is programmed and configured to vary the pressure supplied by the at least one variable pressure source to cyclically supply a continuously varying pressure to each actuator with a pressure cycle time of between about 0.8 sec and about 2.0 sec to advance each actuator, wherein the pressure supplied by the pressure source to each actuator during advancement of that actuator increases continuously from a minimum pressure to a maximum pressure then decreases continuously from the maximum pressure to the minimum pressure.

42. The method of claim 41, further comprising applying a lubricant to the subject's back.

43. The method of claim 41, further comprising repeatedly switching between the continuously varying pressure mode and the step-pulse low frequency mode.

44. The method of claim 41, further comprising switching from the step-pulse low frequency mode to the step-pulse high frequency mode; and removing the tool from the subject's back.

45. A kit for use in treating a spine, comprising:

a physical therapy tool for use in treating a spine, comprising:

at least one variable pressure source, two pairs of pads, wherein each pad is connected to an actuator; and a controller programmed and configured to vary the pressure supplied by the at least one variable pressure source to cyclically supply continuously varying pressure to each actuator to advance each actuator, wherein the pressure supplied by the pressure source to each actuator during advancement of that actuator increases continuously from a minimum pressure to a maximum pressure then decreases continuously from the maximum pressure to the minimum pressure; and a lubricant for applying to a subject's back.

46. The kit of claim 45 further comprising instructions describing at least the operation of the physical therapy tool.

47. The kit of claim 45 further comprising a bench.

48. The kit of claim 47, wherein the bench is an adjustable bench.

* * * * *